(12) United States Patent
Gareau et al.

(10) Patent No.: US 7,439,260 B2
(45) Date of Patent: Oct. 21, 2008

(54) 7-(1,3-THIAZOL-2-YL)THIO-COUMARIN DERIVATIVES AND THEIR USE AS LEUKOTRIENE BIOSYNTHESIS INHIBITORS

(75) Inventors: Yves Gareau, Notre-Dame de L'ile Perrot (CA); Helene Juteau, Laval (CA); D. Bruce MacKay, Dollard-des-Ormeaux (CA); Richard Friesen, Kirkland (CA); Erich L. Grimm, Baie d'Urfe (CA); Marc Blouin, St-Lazare (CA); Sebastien Laliberte, Ile Perrot (CA)

(73) Assignee: Merck Forsst Canada & Co., Quebec (CA)

( * ) Notice: Subject to any disclaimer, the term of this patent is extended or adjusted under 35 U.S.C. 154(b) by 403 days.

(21) Appl. No.: 10/559,885

(22) PCT Filed: Jun. 8, 2004

(86) PCT No.: PCT/CA2004/000861

§ 371 (c)(1),
(2), (4) Date: Dec. 7, 2005

(87) PCT Pub. No.: WO2004/108720

PCT Pub. Date: Dec. 16, 2004

(65) Prior Publication Data

US 2006/0116406 A1    Jun. 1, 2006

Related U.S. Application Data

(60) Provisional application No. 60/477,854, filed on Jun. 11, 2003, provisional application No. 60/511,038, filed on Oct. 14, 2003.

(51) Int. Cl.
*A61K 31/427*     (2006.01)
*A61K 31/44*      (2006.01)
*C07D 277/20*     (2006.01)
*C07D 417/14*     (2006.01)

(52) U.S. Cl. .................. 514/369; 548/146; 548/182; 548/186; 546/268.1; 546/268.4; 546/269.7; 514/336; 514/342; 514/365

(58) Field of Classification Search .......... 548/146, 548/182, 186; 546/268.1, 268.4, 269.7; 514/336, 514/342, 365, 369
See application file for complete search history.

(56) References Cited

U.S. PATENT DOCUMENTS

| 5,169,838 A | * 12/1992 | Samreth et al. ............. 514/27 |
| 5,424,320 A | 6/1995 | Fortin et al. |
| 5,527,827 A | 6/1996 | Delorme et al. |
| 5,552,437 A | 9/1996 | Delorme et al. |

FOREIGN PATENT DOCUMENTS

| WO | WO 96/13491 | 5/1996 |
| WO | WO 96/13500 | 5/1996 |

OTHER PUBLICATIONS

Crawley G., et al, Journal of Medicinal Chemistry, vol. 38, No. 20, pp. 3951-3956, 1995.

* cited by examiner

*Primary Examiner*—Golam M Shameem
(74) *Attorney, Agent, or Firm*—Mollie M. Yang; Valerie J. Camara

(57) ABSTRACT

The instant invention provides compounds of Formula (I) which are leukotriene biosynthesis inhibitors. Compounds of formula (I) are useful as anti-asthmatic, anti-allergic, anti-inflammatory, cytoprotective and anti-artherosclerotic agents.

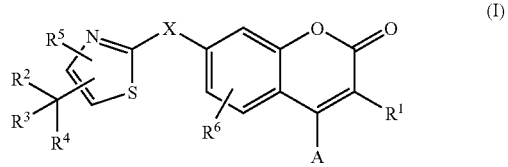

(I)

10 Claims, No Drawings

7-(1,3-THIAZOL-2-YL)THIO-COUMARIN DERIVATIVES AND THEIR USE AS LEUKOTRIENE BIOSYNTHESIS INHIBITORS

CROSS REFERENCE TO RELATED APPLICATIONS

This application is a 35 U.S.C. § 371 filing from International Application No. PCT/CA2004/000861, filed Jun. 8, 2004, which claims the benefit under 35 U.S.C. 119(e) of U.S. Provisional Application No. 60/477,854, filed Jun. 11, 2003 and U.S. Provisional Application No. 60/511,038, filed Oct. 14, 2003.

FIELD OF THE INVENTION

The instant invention involves novel compounds which are useful as inhibitors of leukotriene biosynthesis.

BACKGROUND OF THE INVENTION

Inhibition of leukotriene biosynthesis has been an active area of pharmaceutical research for many years. The leukotrienes constitute a group of locally acting hormones, produced in living systems from arachidonic acid. Leukotrienes are potent contractile and inflammatory mediators derived by enzymatic oxygenation of arachidonic acid by 5-lipoxygenase. One class of leukotriene biosynthesis inhibitors are those known to act through inhibition of 5-lipoxygenase (5-LO).

The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenases on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various diseases states are also discussed in the book by Rokach.

In general, 5-LO inhibitors have been sought for the treatment of allergic rhinitis, asthma and inflammatory conditions including arthritis. One example of a 5-LO inhibitor is the marketed drug zileuton (ZYLOFT®) which is indicated for the treatment of asthma. More recently, it has been reported that 5-LO may be an important contributor to the atherogenic process; see Mehrabian, M. et al., Circulation Research, Jul. 26, 2002 91(2):120-126.

Despite significant therapeutic advances in the treatment and prevention of conditions affected by 5-LO inhibition, further treatment options are needed. The instant invention addresses that need by providing novel 5-LO inhibitors which are useful for inhibiting leukotriene biosynthesis.

SUMMARY OF THE INVENTION

The instant invention relates to compounds of Formula I which are leukotriene biosynthesis inhibitors, methods for their preparation, and methods and pharmaceutical formulations for using these compounds in mammals, especially humans.

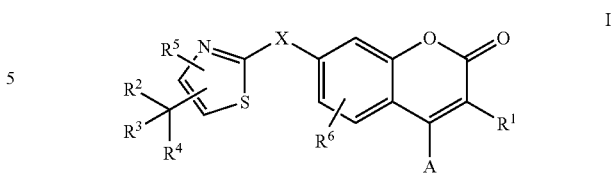

The compounds of Formula I are useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection. The instant invention provides methods of treatment comprising administering a therapeutically effective amount of a compound of Formula I to a patient in need of the above-described treatments.

Additionally, the instant invention involves the use of compounds of Formula I to slow or halt atherogenesis. Therefore, the instant invention also provides a method for treating atherosclerosis, which includes halting or slowing the progression of atherosclerotic disease once it has become clinically evident, comprising administering a therapeutically effective amount of a compound of Formula I to a patient in need of such treatment. The instant invention also provides methods for preventing or reducing the risk of developing atherosclerosis and atherosclerotic disease events, comprising administering a prophylactically effective amount of a compound of Formula I to a patient who is at risk of developing atherosclerosis or having an atherosclerotic disease event. The instant invention further provides the use of a compound of Formula I in combination with other therapeutically effective agents. Additional embodiments will be evident from the following detailed description.

DETAILED DESCRIPTION OF THE INVENTION

The novel leukotriene biosynthesis inhibitors of the instant invention are compounds of structural Formula I

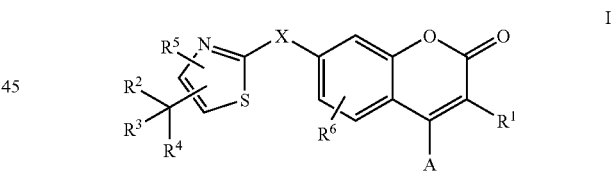

and the pharmaceutically acceptable salts and esters thereof wherein:

$R^1$ is selected from the group consisting of —H, —$C_{1-6}$ alkyl and —$C_{3-6}$ cycloalkyl;

$R^2$ is selected from the group consisting of —H, —OH, —$OC_{1-3}$alkyl, —F and tetrazolyl, provided that when $R^2$ is tetrazolyl then neither $R^3$ nor $R^4$ is Z;

$R^3$ is selected from the group consisting of —H, —$CF_3$, —$CF_2CF_3$, —$C_{1-6}$alkyl, —$C_{1-6}$alkyl substituted with fluoro, —$C_{1-6}$alkyl-$R^7$, —$C_{2-6}$alkenyl, —$C_{3-6}$cycloalkyl, —$C_{5-7}$cycloalkenyl and -Z;

$R^4$ is selected from the group consisting of —H, —$CF_3$, —$CF_2CF_3$, —$C_{1-6}$alkyl, —$C_{1-6}$alkyl substituted with fluoro, —$C_{1-6}$alkyl-$R^7$, —$C_{2-6}$alkenyl, —$C_{3-6}$cycloalkyl, —$C_{5-7}$cycloalkenyl and -Z;

or $R^3$ and $R^4$ are joined together with the carbon to which they are attached to form a ring selected from the group consisting of a —$C_{3-6}$cycloalkyl ring and a —$C_{5-7}$cycloalkenyl ring, provided that when $R^3$ and $R^4$ are joined together with the carbon to which they are attached to form a —$C_{5-7}$ cycloalkenyl ring, there is no double bond at the C1 position in the ring;

or $R^2$ and $R^3$ are joined together to form =$C_{1-6}$alkyl;

or $R^2$, $R^3$ and $R^4$ are joined together with the carbon to which they are attached to form a cycloalkenyl ring selected from:

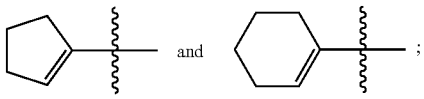

$R^5$ is selected from the group consisting of —H, —$C_{1-6}$ alkyl, —$C_{3-6}$ cycloalkyl and halo;

$R^6$ is selected from the group consisting of —H, —$C_{1-6}$ alkyl, —$C_{3-6}$ cycloalkyl and halo;

$R^7$ is selected from the group consisting of —$COOR^1$, —C(O)H, —CN, —$CR^1R^1OH$, —$OR^1$, —S—$C_{1-6}$alkyl and —S—$C_{3-6}$ cycloalkyl;

A is selected from the group consisting of
a) a 5-membered aromatic ring containing (i) one or more carbon atoms, (ii) one heteroatom selected from oxygen and sulfur, and (iii) zero, one, two or three nitrogen atoms,
b) a 5-membered aromatic ring containing one or more carbon atoms and from one to four nitrogen atoms,
c) a 6-membered aromatic ring containing carbon atoms and one, two or three nitrogen atoms;
d) a 6-membered aromatic ring selected from

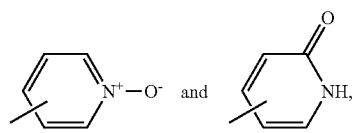

e) a bicyclic aromatic ring system selected from benzothienyl, indolyl, quinolinyl and naphthalenyl;
f) phenyl,
g) —$CH_2$—$R^8$, wherein $R^8$ is selected from phenyl and dioxolanyl,
h) —$C_{3-6}$cycloalkyl,
i) —$C_{5-7}$cycloalkenyl,
j) —$C_{1-6}$alkyl; and
k) —$C_{2-6}$alkenyl, and wherein A is optionally mono- or di-substituted with a substituent independently selected at each occurrence from the group consisting of (i) halo, (ii) —OH, (iii) —$C_{1-3}$allyl optionally substituted with one or more of halo for example including —$CF_3$, (iv) —$OC_{1-3}$alkyl optionally substituted with one or more of halo, (v) —$OC_{3-6}$cycloalkyl, (vi) —$CH_2OH$, (vii) —$COOR^1$, (viii) —CN and (ix) —$NR^9R^{10}$;

$R^9$ is selected from the group consisting of —H, —$C_{1-6}$ alkyl and —$C_{3-6}$ cycloalkyl;

$R^{10}$ is selected from the group consisting of —H, —$C_{1-6}$ alkyl, —$C_{3-6}$ cycloalkyl and —$COOR^1$;

X is selected from the group consisting of —S—, —SO— and —$SO_2$—; and

Z is selected from the group consisting of
a) a 5-membered aromatic ring containing (i) one or more carbon atoms, (ii) one heteroatom selected from oxygen and sulfur, and (iii) zero, one, two or three nitrogen atoms,
b) a 5-membered aromatic ring containing one or more carbon atoms and from one to four nitrogen atoms,
c) a 6-membered aromatic ring containing carbon atoms and one, two or three nitrogen atoms;
d) phenyl, and
e) —$CH_2$—$R^8$, wherein $R^8$ is selected from phenyl and dioxolanyl, and wherein Z is optionally mono- or di-substituted with a substituent independently selected at each occurrence from the group consisting of (i) halo, (ii) —OH, (iii) —$C_{1-3}$alkyl optionally substituted with one or more of halo for example including —$CF_3$, (iv) —$OC_{1-3}$alkyl optionally substituted with one or more of halo, (v) —$OC_{3-6}$cycloalkyl, (vi) —$CH_2OH$, (vii) —$COOR^1$, (viii) —CN and (ix) —$NR^9R^{10}$.

In one embodiment of this invention, $R^1$ is selected from —H and —$C_{1-6}$ alkyl. In a class of this embodiment, $R^1$ is selected from —H and —$CH_3$.

In a second embodiment of this invention, $R^2$ is selected from the group consisting of —H, —OH and —F. In a class of this embodiment, $R^2$ is selected from —H and —OH.

In a third embodiment of this invention, $R^3$ is selected from the group consisting of —$C_{1-6}$alkyl optionally substituted with fluoro, —$C_{1-6}$alkyl-$R^7$, and —$C_{3-6}$cycloalkyl. In a class of this embodiment, $R^3$ is selected from —$C_{1-2}$alkyl optionally substituted with fluoro, particularly —$CF_3$, —$CH_3$ and —$C_2H_5$, and cyclopropyl.

In a fourth embodiment of this invention, $R^4$ is selected from the group consisting of —$C_{1-6}$alkyl optionally substituted with fluoro, —$C_{1-6}$alkyl-$R^7$, —$C_{2-6}$alkenyl, —$C_{3-6}$cycloalkyl and -Z. In a class of this embodiment, $R^4$ is selected from —$C_{1-2}$alkyl optionally substituted with fluoro, particularly —$CF_3$, —$CH_3$ and —$C_2H_5$, and cyclopropyl.

In a fifth embodiment, $R^3$ and $R^4$ are joined together with the carbon to which they are attached to form a —$C_{3-6}$cycloalkyl ring.

In a sixth embodiment of this invention, $R^5$ is selected from —H and —$CH_3$. In a class of this embodiment, $R^5$ is —H.

In a seventh embodiment of this invention, $R^6$ is selected from the group consisting of —H and —$CH_3$. In a class of this embodiment, $R^6$ is —H.

In an eighth embodiment of this invention, A is unsubstituted, mono- or di-substituted as described in Formula I and is selected from the group consisting of:
a) a 5-membered aromatic ring containing (i) one or more carbon atoms, (ii) one heteroatom selected from oxygen and sulfur, and (iii) zero, one, two or three nitrogen atoms,
b) a 5-membered aromatic ring containing one or more carbon atoms and from one to four nitrogen atoms,
c) a 6-membered aromatic ring containing carbon atoms and one, two or three nitrogen atoms; and
d) phenyl.

In a class of this embodiment, A is unsubstituted, mono- or di-substituted and is selected from the group consisting of thienyl, furanyl, oxazolyl, thiazolyl, tetrazolyl, pyridinyl and phenyl. In a sub-class of this embodiment, A is selected from phenyl, 3-fluorophenyl, 4-fluoro-phenyl, unsubstituted or mono-substituted thiazolyl, and unsubstituted or mono-substituted pyridinyl. More particularly, A is 4-fluoro-phenyl.

In a ninth embodiment of this invention, Z is unsubstituted, mono- or di-substituted as described in Formula I and is selected from the group consisting of phenyl, benzyl, pyridinyl, thiazolyl, dioxolanyl and tetrazolyl. In a class of this embodiment, Z is unsubstituted, mono- or di-substituted and is selected from the group consisting of phenyl, pyridinyl and thiazolyl.

In a tenth embodiment of this invention are compounds of Formula I having structural Formula Ia

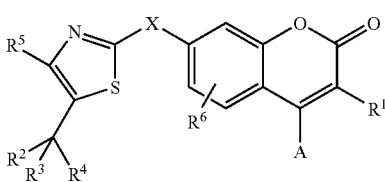

Ia and the pharmaceutically acceptable salts and esters thereof wherein the definitions of $R^1$, $R^2$, $R^3$, $R^4$, $R^5$, $R^6$, X and A are as defined above in Formula I, and additionally encompassing each of the embodiments one through nine described above.

In an eleventh embodiment of this invention are compounds of Formula I having structural Formula Ib

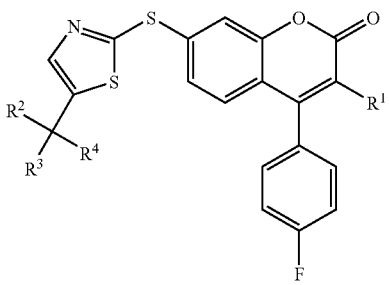

Ib and the pharmaceutically acceptable salts and esters thereof wherein:
$R^1$ is selected from the group consisting of —H and —CH$_3$;
$R^2$ is selected from the group consisting of —H and —OH;
$R^3$ is selected from the group consisting of —CF$_3$ and —C$_{1-6}$alkyl optionally substituted with fluorine;
$R^4$ is selected from the group consisting of —CF$_3$ and —C$_{1-6}$alkyl optionally substituted with fluorine;
or $R^3$ and $R^4$ are joined together with the carbon to which they are attached to form C$_{4-6}$cycloalkyl.

Compounds of this invention include but are not limited to the following:
4-(4-fluorophenyl)-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-({5-[2,2,2-trifluoro-1-hydroxy-1-(trifluoromethyl)ethyl]-1,3-thiazol-2-yl}sulfonyl)-2H-chromen-2-one;
4-(4-fluorophenyl)-7-({5-[2,2,2-trifluoro-s-hydroxy-1-(trifluoromethyl)ethyl]-1,3-thiazol-2-yl}sulfinyl)-2H-chromen-2-one;
4-(4-methylphenyl)-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-[(4-methyl-1,3-thiazol-2-yl)thio]-2H-chromen-2-one;
4-(4-fluorophenyl)-7-({4-methyl-5-[2,2,2-trifluoro-1-hydroxy-1-(trifluoromethyl)ethyl]-1,3-thiazol-2-yl}thio)-2H-chromen-2-one;
4-(4-methoxyphenyl)-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-({5-[1-hydroxy-1-(1,3-thiazol-2-yl)propyl]-1,3-thiazol-2-yl}thio)-2H-chromen-2-one;
4-(3-thienyl)-7-({5-[2,2,2-trifluoro-1-hydroxy-1-(trifluoromethyl)ethyl]-1,3-thiazol-2-yl}thio)-2H-chromen-2-one;
4-ethyl-7-({5-[2,2,2-trifluoro-1-hydroxy-1-(trifluoromethyl)ethyl]-1,3-thiazol-2-yl}thio)-2H-chromen-2-one;
4-fluoro-7-{[5-(1-hydroxy-1-methylethyl)-1,3-thiazol-2-yl]thio}-2H-chromen-2-one;
4-(4-fluoro-3-methylphenyl)-7-({5-[2,2,2-trifluoro-1-hydroxy-1-(trifluoromethyl)ethyl]-1,3-thiazol-2-yl}thio)-2H-chromen-2-one;
4-(4-ethoxyphenyl)-7-({5-[2,2,2-trifluoro-1-hydroxy-1-(trifluoromethyl)ethyl]-1,3-thiazol-2-yl}thio)-2H-chromen-2-one;
4-phenyl-7-({5-[2,2,2-trifluoro-1-hydroxy-1-(trifluoromethyl)ethyl]-1,3-thiazol-2-yl}thio)-2H-chromen-2-one;
4-cyclopropyl-7-({5-[2,2,2-trifluoro-1-hydroxy-1-(trifluoromethyl)ethyl]-1,3-thiazol-2-yl}thio)-2H-chromen-2-one;
4-pyridin-3-yl-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-{[5-(1-hydroxycyclobutyl)-1,3-thiazol-2-yl]thio}-2H-chromen-2-one;
4-(2-methylphenyl)-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-({5-[1-hydroxy-1-(1,3-thiazol-2-yl)propyl]-1,3-thiazol-2-yl}sulfonyl)-2H-chromen-2-one;
4-3-(methylphenyl)-7-({5-[2,2,2-trifluoro-1-hydroxy-1-(trifluoromethyl)ethyl]-1,3-thiazol-2-yl)thio}-2H-chromen-2-one;
4-benzyl-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-{[5-(1-hydroxy-1-phenylpropyl)-1,3-thiazol-2-yl]thio}-2H-chromen-2-one;
4-(4-fluorophenyl)-7-{[5-(1-hydroxy-1-pyridin-2-ylethyl)-1,3-thiazol-2-yl]thio}-2H-chromen-2-one;
4-(4-fluorophenyl)-7-({5-[1-hydroxy-1-(1,3-thiazol-2-yl)propyl]-1,3-thiazol-2-yl}sulfinyl)-2H-chromen-2-one;
4-(2-methyl-1,3-thiazol-4-yl)-7-({5-[2,2,2-trifluoro-1-hydroxy-1-(trifluoromethyl)ethyl]-1,3-thiazol-2-yl{thio)-2H-chromen-2-one;
4-(4-fluorophenyl)-7-({5-[2,2,2-trifluoro-1-methoxy-1-(trifluoromethyl)ethyl]-1,3-thiazol-2-yl}thio)-2H-chromen-2-one;
4-(4-fluorophenyl)-7-{[5-(1-hydroxy-1-phenylethyl)-1,3-thiazol-2-yl]thio}-2H-chromen-2-one;
4-(3-fluorophenyl)-7-({5-[2,2,2-trifluoro-1-hydroxy-1-(trifluoromethyl)ethyl]-1,3-thiazol-2-yl}thio)-2H-chromen-2-one;
4-cyclohexyl-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-{[5-(1-hydroxycyclopentyl)-1,3-thiazol-2-yl]thio}-2H-chromen-2-one;
4-(3-fluoro-4-methylphenyl)-7-({5-[2,2,2-trifluoro-1-hydroxy-1-(trifluoromethyl)ethyl]-1,3-thiazol-2-yl}thio)-2H-chromen-2-one;
4-(4-fluorophenyl)-7-{[5-(2,2,2-trifluoro-1-hydroxy-1-phenylethyl)-1,3-thiazol-2-yl]thio}-2H-chromen-2-one;

4-[2-oxo-7-({5-[2,2,2-trifluoro-1-hydroxy-1-(trifluoromethyl)ethyl]-1,3-thiazol-2-yl}thio)-2H-chromen-4-yl]benzonitrile;

3-[2-oxo-7-({5-[2,2,2-trifluoro-1-hydroxy-1-(trifluoromethyl)ethyl]-1,3-thiazol-2-yl}thio)-2H-chromen-4-yl]benzonitrile;

4-(1-benzothien-2-yl)-7-({5-[2,2,2-trifluoro-1-hydroxy-1-(trifluoromethyl)ethyl]-1,3-thiazol-2-yl}thio)-2H-chromen-2-one;

4-(3-fluoro-2-methylphenyl)-7-{5-[2,2,2-trifluoro-1-hydroxy-1-(trifluoromethyl)ethyl]-1,3-thiazol-2-yl}thio)-2H-chromen-2-one;

7-{[5-(1-ethylpropyl)-1,3-thiazol-2-yl]thio}-4-(4-fluorophenyl)-2H-chromen-2-one;

4-(2-methyl-1,3-oxazol-4-yl)-7-{5-[2,2,2-trifluoro-1-hydroxy-1-(trifluoromethyl)ethyl]-1,3-thiazol-2-yl}thio)-2H-chromen-2-one;

methyl 4-[2-oxo-7-({5-[2,2,2-trifluoro-1-hydroxy-1-(trifluoromethyl)ethyl]-1,3-thiazol-2-yl}thio)-2H-chromen-4-yl]benzoate;

7-{[5-(1-benzyl-2,2,2-trifluoro-1-hydroxyethyl)-1,3-thiazol-2-yl]thio}-4-(4-fluorophenyl)-2H-chromen-2-one;

7-({5-[1-(4-chlorophenyl)-2,2,2-trifluoro-1-hydroxyethyl]-1,3-thiazol-2-yl}-thio)-4-(4-fluorophenyl)-2H-chromen-2-one;

4-[4-(dimethylamino)phenyl]-7-({5-[2,2,2-trifluoro-1-hydroxy-1-(trifluoromethyl)ethyl]-1,3-thiazol-2-yl}thio)-2H-chromen-2-one;

4-(4-fluorophenyl)-7-({5-[1-hydroxy-1-(trifluoromethyl)propyl]-1,3-thiazol-2-yl}thio)-2H-chromen-2-one;

4-(3-isopropylphenyl)-7-({5-[2,2,2-trifluoro-1-hydroxy-1-(trifluoromethyl)ethyl]-1,3-thiazol-2-yl}thio)-2H-chromen-2-one;

4-(4-fluorophenyl)-7-({5-[2,2,2-trifluoro-1-(4-fluorophenyl)-1-hydroxyethyl]-1,3-thiazol-2-yl}thio)-2H-chromen-2-one;

4-(4-fluorophenyl)-3-methyl-7-({5-[2,2,2-trifluoro-1-hydroxy-1-(trifluoromethyl)ethyl]-1,3-thiazol-2-yl}thio)-2H-chromen-2-one;

4-[2-(hydroxymethyl)phenyl]-7-({5-[2,2,2-trifluoro-1-hydroxy-1-(trifluoromethyl)ethyl]-1,3-thiazol-2-yl}thio)-2H-chromen-2-one;

7-({5-[2,2,2-trifluoro-1-hydroxy-1-(trifluoromethyl)ethyl]-1,3-thiazol-2-yl}thio)-4-[2-(trifluoromethyl)phenyl]-2H-chromen-2-one;

4-(1,3-thiazol-4-yl)-7-({5-[2,2,2-trifluoro-1-hydroxy-1-(trifluoromethyl)ethyl]-1,3-thiazol-2-yl}thio)-2H-chromen-2-one;

4-(2-methylphenyl)-7-({5-[2,2,2-trifluoro-1-hydroxy-1-(trifluoromethyl)ethyl]-1,3-thiazol-2-yl}sulfinyl)-2H-chromen-2-one;

4-(4-fluorophenyl)-7-[(5-isopropyl-1,3-thiazol-2-yl)thio]-2H-chromen-2-one;

4-(2-methylphenyl)-7-({5-[2,2,2-trifluoro-1-hydroxy-1-(trifluoromethyl)ethyl]-1,3-thiazol-2-yl]sulfonyl)-2H-chromen-2-one;

4-(2-amino-1,3-thiazol-4-yl)-7-({5-[2,2,2-trifluoro-1-hydroxy-1-(trifluoromethyl)ethyl]-1,3-thiazol-2-yl}thio)-2H-chromen-2-one;

4-(4-fluorophenyl)-7-({5-[(1S)-1-hydroxy-1-(trifluoromethyl)propyl]-1,3-thiazol-2-yl}thio)-2H-chromen-2-one;

4-propyl-7-({5-[2,2,2-trifluoro-1-hydroxy-1-(trifluoromethyl)ethyl]-1,3-thiazol-2-yl}thio)-2H-chromen-2-one;

N-{3-[2-oxo-7-({5-[2,2,2-trifluoro-1-hydroxy-1-(trifluoromethyl)ethyl]-1,3-thiazol-2-yl}thio)-2H-chromen-4-yl]phenyl}acetamide;

3-ethyl-4-(4-fluorophenyl)-7-({5-[2,2,2-trifluoro-1-hydroxy-1-(trifluoromethyl)ethyl]-1,3-thiazol-2-yl}thio)-2H-chromen-2-one;

4-(3-furyl)-7-({5-[1-hydroxy-1-(trifluoromethyl)propyl]-1,3-thiazol-2-yl}thio)-3-methyl-2-chromen-2-one;

4-(6-methylpyridin-3-yl)-7-({5-[2,2,2-trifluoro-1-hydroxy-1-(trifluoromethyl)ethyl]-1,3-thiazol-2-yl}thio)-2H-chromen-2-one;

4-(4-fluorophenyl)-7-({5-[(1E and Z)-1-methylprop-1-en-1-yl]-1,3-thiazol-2-yl}thio)-2H-chromen-2-one 7-[(5-sec-butyl-1,3-thiazol-2-yl)thio]-4-(4-fluorophenyl)-2H-chromen-2-one;

4-(4-fluorophenyl)-7-{[5-(2,2,2-trifluoro-1-hydroxy-1-methylethyl)-1,3-thiazol-2-yl]thio}-2H-chromen-2-one;

4-[3-(difluoromethoxy)phenyl]-7-({5-[2,2,2-trifluoro-1-hydroxy-1-(trifluoromethyl)ethyl]-1,3-thiazol-2-yl}thio)-2H-chromen-2-one;

4-(4-fluorophenyl)-7-({5-[1-hydroxy-2-methyl-1-(trifluoromethyl)propyl]-1,3-thiazol-2-yl}thio)-2H-chromen-2-one;

7-({5-[1-hydroxy-1-(trifluoromethyl)propyl]-1,3-thiazol-2-yl}thio)-4-(4-propylphenyl)-2H-chromen-2-one;

7-({5-[1-hydroxy-1-(trifluoromethyl)propyl]-1,3-thiazol-2-yl}thio)-4-[3-(trifluoromethoxy)phenyl]-2H-chromen-2-one;

7-{[5-(1-cyclopropyl-2,2,2-trifluoro-1-hydroxyethyl)-1,3-thiazol-2-yl]thio}-4-(4-fluorophenyl)-2H-chromen-2-one;

7-{[4-(1-ethyl-1-hydroxypropyl)-1,3-thiazol-2-yl]thio}-4-(4-fluorophenyl)-2H-chromen-2-one;

7-({5-[1-(1,3-dioxolan-2-ylmethyl)-2,2,2-trifluoro-1-hydroxyethyl]-1,3-thiazol-2-yl}thio)-4-(4-fluorophenyl)-2H-chromen-2-one;

4-[3-(difluoromethoxy)phenyl]-7-({5-[1-hydroxy-1-(trifluoromethyl)propyl]-1,3-thiazol-2-yl}thio)-2H-chromen-2-one;

4-(4-fluorophenyl)-7-({5-[1-hydroxy-2,2-dimethyl-1-(trifluoromethyl)propyl]-1,3-thiazol-2-yl}thio)-2H-chromen-2-one;

4-(3,5-dichlorophenyl)-7-({5-[1-hydroxy-1-(trifluoromethyl)propyl]-1,3-thiazol-2-yl}thio)-2H-chromen-2-one;

(−)-7-{[5-(1-cyclopropyl-2,2,2-trifluoro-1-hydroxyethyl)-1,3-thiazol-2-yl]thio}-4-(4-fluorophenyl)-2H-chromen-2-one;

(+)-7-{[5-(1-cyclopropyl-2,2,2-trifluoro-1-hydroxyethyl)-1,3-thiazol-2-yl]thio}-4-(4-fluorophenyl)-2H-chromen-2-one;

7-({5-[(1S)-1-hydroxy-1-(trifluoromethyl)propyl]-1,3-thiazol-2-yl}thio)-4-phenyl-2H-chromen-2-one;

7-({5-[(1R)-1-hydroxy-1-(trifluoromethyl)propyl]-1,3-thiazol-2-yl}thio)-4-phenyl-2H-chromen-2-one;

7-{[5-(1-cyclopropyl-2,2,2-trifluoro-1-hydroxyethyl)-1,3-thiazol-2-yl]sulfonyl}-4-(4-fluorophenyl)-2H-chromen-2-one;

7-{[5-(1-cyclopropyl-2,2,2-trifluoro-1-hydroxyethyl)-1,3-thiazol-2-yl]sulfonyl}-4-(4-fluorophenyl)-2H-chromen-2-one;

7-({5-[1-hydroxy-1-(trifluoromethyl)propyl]-1,3-thiazol-2-yl}thio)-4-(6-methylpyridin-3-yl)-2H-chromen-2-one;

7-{[5-(1-cyclopropyl-2,2,2-trifluoro-1-hydroxyethyl)-1,3-thiazol-2-yl]sulfinyl}-4-(4-fluorophenyl)-2H-chromen-2-one;

7-{[5-(1-cyclopropyl-2,2,2-trifluoro-1-hydroxyethyl)-1,3-thiazol-2-yl]sulfonyl}(4-fluorophenyl)-2H-chromen-2-one;

7-({5-[dicyclopropyl(hydroxy)methyl]-1,3-thiazol-2-yl}thio)-4-phenyl-2H-chromen-2-one;

7-({5-[dicyclopropyl(hydroxy)methyl]-1,3-thiazol-2-yl}sulfinyl)-4-(4-fluorophenyl)-2H-chromen-2-one;
7-({5-[dicyclopropyl(hydroxy)methyl]-1,3-thiazol-2-yl}sulfonyl)-4-(4-fluorophenyl)-2H-chromen-2-one;
7-({5-[dicyclopropyl(hydroxy)methyl]-1,3-thiazol-2-yl}thio)-4-(4-fluorophenyl)-8-methyl-2H-chromen-2-one;
7-({5-[dicyclopropyl(hydroxy)methyl]-methyl-1,3-thiazol-2-yl}thio)-4-(4-fluorophenyl)-2H-chromen-2-one;
7-[(4-methyl-1,3-thiazol-2-yl)thio]-4-pyridin-3-yl-2H-chromen-2-one;
7-({5-[dicyclopropyl(hydroxy)methyl]-4-methyl-1,3-thiazol-2-yl}thio)-4-pyridin-3-yl-2H-chromen-2-one;
(3R)-4,4,4-trifluoro-3-(2-{[4-(4-fluorophenyl)-2-oxo-2H-chromen-7-yl]thio}-1,3-thiazol-5-yl)-3-hydroxybutanal;
3-(7-{[5-(1-cyclopropyl-2,2,2-trifluoro-1-hydroxyethyl)-1,3-thiazol-2-yl]thio}-2-oxo-2H-chromen-4-yl)pyridin-2(1H)-one;
5-(7-{[5-(1-cyclopropyl-2,2,2-trifluoro-1-hydroxyethyl)-1,3-thiazol-2-yl]thio}-2-oxo-2H-chromen-4-yl)pyridin-2(1H)-one;
4-(4-fluorophenyl)-7-({5-[hydroxy(diphenyl)methyl]-1,3-thiazol-2-yl}thio)-2H-chromen-2-one;
7-{[5-(dicyclopropylmethyl)-1,3-thiazol-2-yl]thio}-4-(4-fluorophenyl)-2H-chromen-2-one;
7-({[5-(1-ethylprop-1-en-1-yl)-1,3-thiazol-2-yl]amino}methyl)-4-(6-fluoro-1-oxidopyridin-3-yl)-2H-chromen-2-one;
7-{[5-(dicyclopropylmethyl)-1,3-thiazol-2-yl]thio}-4-pyridin-3-yl-2H-chromen-2-one;
7-({5-[dicyclopropyl(hydroxy)methyl]-1,3-thiazol-2-yl}thio)-4-(3-methylphenyl)-2H-chromen-2-one;
7-{[5-(1-cyclopropyl-2,2,2-trifluoro-1-hydroxyethyl)-1,3-thiazol-2-yl]thio}-4-(3-methylphenyl)-2H-chromen-2-one;
7-({5-[cyclopropyl(hydroxy)phenylmethyl]-1,3-thiazol-2-yl}thio)-4-pyridin-3-yl-2H chromen-2-one;
7-({5-[dicyclopropyl(hydroxy)methyl]-1,3-thiazol-2-yl}thio)-4-(3,5-dimethylphenyl)-2H-chromen-2-one;
7-{[5-1-fluoro-1-methylpropyl)-1,3-thiazol-2-yl]thio}-4-(4-fluorophenyl)-2H-chromen-2-one;
7-({5-[dicyclopropyl(hydroxy)methyl]-1,3-thiazol-2-yl}thio)-4-(2-methyl-1,3-thiazol-4-yl)-2H-chromen-2-one;
7-{[5-(dicyclopropylmethyl)-1,3-thiazol-2-yl]thio}-4-phenyl-2H-chromen-2-one;
7-({5-[dicyclopropyl(hydroxy)methyl]-1,3-thiazol-2-yl}thio)-4-(3,5-dimethoxyphenyl)-2H-chromen-2-one;
7-({5-[dicyclopropyl(hydroxy)methyl]-1,3-thiazol-2-yl}thio)-4-[3-(hydroxymethyl)phenyl]-2H-chromen-2-one;
7-([5-(1-ethyl-1-hydroxypropyl)-1,3-thiazol-2-yl]thio}-4-pyridin-3-yl-2H-chromen-2-one;
7-({5-[1-ethyl-1-(2H-tetrazol-2-yl)propyl]-1,3-thiazol-2-yl}thio)-4-pyridin-3-yl-2H-chromen-2-one;
7-({5-[1-ethyl-1-(1H-tetrazol-1-yl)propyl]-1,3-thiazol-2-yl}thio)-4-pyridin-3-yl-2H-chromen-2-one;
7-({5-[dicyclopropyl(hydroxy)methyl]-1,3-thiazol-2-yl}thio)-4-(3-hydroxyphenyl)-2H-chromen-2-one;
7-{[5-(dicyclopropylmethyl)-1,3-thiazol-2-yl]thio}-4-(3-methylphenyl)-2H-chromen-2-one;
7-{[5-(dicyclopropylmethyl)-1,3-thiazol-2-yl]thio}-4-(3,5-dimethylphenyl)-2H-chromen-2-one;
7-({5-[dicyclopropyl(hydroxy)methyl]-1,3-thiazol-2-yl}thio)-4-pyrimidin-5-yl-2H-chromen-2-one;
4-(3,5-dichlorophenyl)-7-({5-[dicyclopropyl(hydroxy)methyl]-1,3-thiazol-2-yl}thio)-2H-chromen-2-one;
4-(3-chlorophenyl)-7-({5-[dicyclopropyl(hydroxy)methyl]-1,3-thiazol-2-yl}thio)-2H-chromen-2-one;
7-([5-(1-ethyl-1-fluoropropyl)-1,3-thiazol-2-yl]thio}-4-(4-fluorophenyl)-2H-chromen-2-one;
7-[(5-cyclopent-1-en-1-yl-1,3-thiazol-2-yl)thio]-4-(4-fluorophenyl)-2H-chromen-2-one;
3-[7-({5-[dicyclopropyl(hydroxy)methyl]-1,3-thiazol-2-yl}thio)-2-oxo-2H-chromen-4-yl]benzonitrile;
7-({5-[(1R)-1-hydroxy-1-(trifluoromethyl)propyl]-1,3-thiazol-2-yl}thio)-4-(3-methylphenyl)-2H-chromen-2-one;
(+)-(S)-4-(4-fluorophenyl)-7-({5-[1-hydroxy-1-(trifluoromethyl)propyl]-1,3-thiazol-2-yl}thio)-2H chromen-2-one;
(-)-(R)-4-(4-fluorophenyl)-7-({5-[1-hydroxy-1-(trifluoromethyl)propyl]-1,3-thiazol-2-yl}thio)-2H chromen-2-one;
7-({5-[dicyclopropyl(hydroxy)methyl]-1,3-thiazol-2-yl}thio)-4-(4-fluorophenyl)-2H-chromen-2-one;
7-({5-[dicyclopropyl(hydroxy)methyl]-1,3-thiazol-2-yl}thio)-4-pyridin-3-yl-2H-chromen-2-one;
7-({5-[1,3-dihydroxy-1-(trifluoromethyl)propyl]-1,3-thiazol-2-yl}thio)-4-(4-fluorophenyl)-2H-chromen-2-one;
7-({5-[(1R)1,3-dihydroxy-1-(trifluoromethyl)propyl]-1,3-thiazol-2-yl}thio)-4-(4-fluorophenyl)-2H-chromen-2-one;
(+)-(3R)-4,4,4-trifluoro-3-(2-{[4-(4-fluorophenyl)-2-oxo-2H-chromen-7-yl]thio}-1,3-thiazol-5-yl)-3-hydroxybutanoic acid;
(-)-(3S)-4,4,4-trifluoro-3-(2-{[4-(4-fluorophenyl)-2-oxo-2H-chromen-7-yl]thio}-1,3-thiazol-5-yl)-3-hydroxybutanoic acid
7-{[5-(1-methylpropyl)-1,3-thiazol-2-yl]thio}-4-(4-fluorophenyl)-2H-chromen-2-one;
(+)-7-{[5-(1-cyclopropyl-2,2,2-trifluoro-1-hydroxyethyl)-1,3-thiazol-2-yl]thio}-4-pyridin-3-ul-2H-chromen-2-one;
(-)-7-{[5-(1-cyclopropyl-2,2,2-trifluoro-1-hydroxyethyl)-1,3-thiazol-2-yl]thio}-4-pyridin-3-ul-2H-chromen-2-one;
4-(4-fluorophenyl)-8-methyl-7-({5-[2,2,2-trifluoro-1-hydroxy-1-(trifluoromethyl)ethyl]-1,3-thiazol-2-yl}thio)-2H-chromen-2-one;
4-(3,5-difluorophenyl)-7-({5-[1-hydroxy-1(trifluoromethyl)propyl]-1,3-thiazol-2-yl}thio)-2H-chromem-2-one;
4-[3-(cyclopropyloxy)phenyl]-7-({5-[1-hydroxy-1-(trifluoromethyl)propyl]-1,3-thiazol-2-yl}thio)-2H-chromen-2-one;
4-(3-methoxyphenyl)-7-({5-[2,2,2-trifluoro-1-hydroxy-1-(trifluoromethyl)propyl]-1,3-thiazol-2-yl}thio-2H-chromen-2-one;
7-({5-[(1R)-hydroxy-1-(trifluoromethyl)propyl]-1,3-thiazol-2-yl}thio)-4-(3-methoxyphenyl)-2H-chromen-2-one;
7-({5-[(1R)-hydroxy-1-(trifluoromethyl)propyl]-1,3-thiazol-2-yl}thio)-4-pyridin-3-yl-2H-chromen-2-one;
4-(4-fluorophenyl)-7-({5-[1-hydroxy-1-(trifluoromethyl)prop-2-en-1-yl]-1,3-thiazol-2-yl}thio)-2H-chromen-2-one;
7-({5-[1-hydroxy-1-(trifluoromethyl)propyl]-1,3-thiazol-2-yl}thio)-4-(2-methyl-1,3-thiazol-4-yl)-2H-chromen-2-one;
4-(4-fluorophenyl)-7-({5-[(1R)-1-hydroxy-1-(trifluoromethyl)propyl]-1,3-thiazol-2-yl}sulfinyl)-2H-chromen-2-one; and
4-(4-fluorophenyl)-7-({5-[(1R)-1-hydroxy-1-(trifluoromethyl)propyl]-1,3-thiazol-2-yl}sulfonyl)-2H-chromen-2-one;

and the pharmaceutically acceptable salts and esters thereof, where appropriate.

Reference to the compounds of this invention as those of "Formula I," "Formula Ia," and "Formula Ib" is intended herein to encompass compounds falling within the scope of each of these structural formulas including pharmaceutically acceptable salts and esters thereof where such salts and esters are possible. The term "pharmaceutically acceptable salts" refers to salts prepared from pharmaceutically acceptable non-toxic bases, such as for example, a sodium salt which could be prepared using NaOH. Pharmaceutically acceptable esters of available hydroxy or carboxylic acid groups can optionally be formed as well. Examples of pharmaceutically acceptable esters include, but are not limited to, —$C_{1-4}$ alkyl and —$C_{1-4}$ alkyl substituted with phenyl-, dimethylamino- and acetylamino.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof. Furthermore, some of the crystalline forms of compounds of the present invention may exist as polymorphs and as such are intended to be included in the present invention. In addition, some of the compounds of the instant invention may form solvates with water or common organic solvents. Such solvates and hydrates are likewise encompassed within the scope of this invention. Some of the compounds described herein contain olefinic double bonds. The invention includes both E and Z geometric isomers.

Compounds of this invention may be separated into their individual diastereoisomers by, e.g., fractional crystallization from suitable solvents, e.g., methylene chloride/hexanes or EtOAc/hexanes, or via chiral chromatography using an optically active stationary phase. Absolute stereochemistry may be determined by X-ray crystallography of crystalline products or crystalline intermediates which are derivatized, if necessary, with a reagent containing a stereogenic center of known configuration. Alternatively, any stereoisomer of a compound of the general formula I may be obtained by stereospecific synthesis using optically pure starting materials or reagents of known absolute configuration.

As used herein "alkyl" is intended to include both branched- and straight-chain saturated aliphatic hydrocarbon groups having the specified number of carbon atoms, e.g., methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like. "Cycloalkyl" means a monocyclic saturated carbocyclic ring, having the specified number of carbon atoms, e.g., 3, 4, 5 or 6 carbon atoms. Examples of cycloalkyl include cyclopropyl, cyclobutyl, cyclopentyl and cyclohexyl.

The term "$C_{2-6}$ alkenyl" as used herein, refers to a straight or branched 2-6 carbon chain with at least one carbon-carbon double bond. Examples of alkenyl include, but are not limited to, vinyl (—CH=$CH_2$), allyl, isopropenyl, pentenyl, hexenyl, heptenyl, 1-propenyl, 2-butenyl, 2-methyl-2-butenyl, and the like. The term "$C_{5-7}$ cycloalkenyl" as used herein means a non-aromatic monocyclic ring having from 5 to 7 carbon atoms in the ring with at least one carbon-carbon double bond.

Within the definition for Formula I, $R^3$ and $R^4$ can be joined together with the carbon to which they are attached to form a —$C_{5-7}$cycloalkenyl ring wherein there is no double bond at the C1 position in the ring. The C1 position is intended to be the ring carbon that bonds the cycloalkenyl ring to the core thiazolyl ring in structural Formula I. In this situation, C1 is also bonded to $R^2$. This is illustrated below using the example where $R^3$ and $R^4$ are joined together with the carbon to which they are attached to form a 3,4-cyclopentenyl ring, see (a):

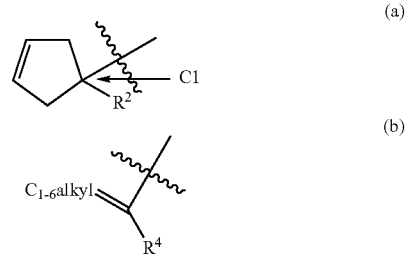

Within the definition for Formula I, $R^2$ and $R^3$ can be joined together to form =$C_{1-6}$alkyl. This is illustrated above, see (b).

Use of the term "optionally" is intended to mean that the genus encompasses compounds containing the specified optional moiety as well as compounds that do not contain such moiety. Each variable is independently defined each time it occurs within the Formula I definitions. For example, when $R^7$ is —$CR^1R^1OH$, $R^1$ is independently selected at each occurrence and they can be the same or different.

Use of the term "substituted" is intended to encompass mono- and poly-substitution on the specified moiety, unless mono- or di-substitution is specified. A mono-substituted moiety has one substituent, while a poly-susbtituted moiety has more than one substituent wherein each carbon atom that is available for substitution in the moiety may independently be unsubstituted, mono- or poly-substituted and which results in the creation of a stable structure. For example, "—$C_{1-6}$ alkyl optionally substituted with fluoro" includes —$CH_3$, —$CH_2F$, —$CHF_2$ and —$CF_3$.

The terms "halo" or "halogen" are meant to include fluoro, chloro, bromo and iodo, unless otherwise noted. Fluoro and chloro are preferred, and fluoro is most preferred.

Examples of 5-membered aromatic rings within the definitions of A and Z include but are not limited to thienyl, furanyl, oxazolyl, thiazolyl, pyrrolyl, pyrazolyl, imidazolyl, and tetrazolyl, represented by the structural formulas below:

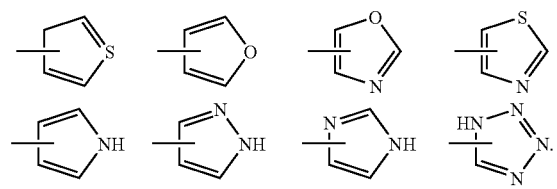

Examples of 6-membered aromatic rings comprised of carbon and one, two or three of —N— within the definition of A and Z include but are not limited to pyridinyl, pyrimidinyl, pyrazinyl and triazinyl represented by the structural formulas below:

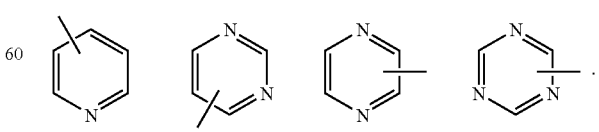

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, and 17) proliferation of myoblastic leukemia cells.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684.

In particular, the compounds of the invention would be useful to reduce the gastric erosion caused by co-administration of a cyclooxygenase-2 selective inhibitor and low-dose aspirin. Cyclooxygenase-2 selective inhibitors are widely used as effective anti-inflammatory drugs with less potential for gastrointestinal complications as compared to traditional, non-selective non-steroidal anti-inflammatory drugs. However, the combined use of a cyclooxygenase-2 selective inhibitor with low-dose aspirin for cardio protection may compromise the gastrointestinal safety of this class of compounds. By virtue of its activity as a 5-lipoxygenase inhibitor, the compounds of the invention would be expected to be gastric protective in this regard. See Fiorucci, et al. FASEB J. 17:1171-1173, 2003. Cyclooxygenase-2 selective inhibitors for use with the invention include but are not limited to rofecoxib (VIOXX®), etoricoxib (ARCOXIA™), celecoxib (CELEBREX®) and valdecoxib (BEXTRA™). A compound of this invention in combination with a cyclooxygenase-2 selective inhibitor could be administered in unit dosage form or separately to a patient on low-dose aspirin therapy. Alternatively, the cyclooxygenase-2 inhibitor could be administered in unit dosage form with low-dose aspirin, in which case a compound of this invention would be administered separately. All three active ingredients in unit dosage form is also encompassed. Conventional dosage amounts of the cyclooxygenase-2 selective inhibitor and aspirin (for cardio protection) may be utilized. For example, rofecoxib could be administered at 12.5 mg, 25 mg or 50 mg once daily. Aspirin could be administered at 81 mg once daily.

In addition, the compounds of this invention can also be used for the treatment of chronic obstructive pulmonary disease (COPD). As described in S. Kilfeather, Chest, 2002, vol 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD.

The compounds of Formula I can also be used for the treatment of atherosclerosis comprising administering a therapeutically effective amount of a compound of Formula I to a patient in need of such treatment. A further aspect of this invention involves a method for preventing or reducing the risk of developing atherosclerosis, comprising administering a prophylactically effective amount of a compound of Formula I to a patient in need-of such treatment. Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of Formula I of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may already have atherosclerotic disease at the time of administration, or may be at risk for developing it.

The method of this invention serves to prevent or slow new atherosclerotic lesion or plaque formation, and to prevent or slow progression of existing lesions or plaques, as well as to cause regression of existing lesions or plaques. Accordingly, one aspect of this invention involves a method for halting or slowing the progression of atherosclerosis, including halting or slowing atherosclerotic plaque progression, comprising administering a therapeutically effective amount of a compound of Formula I to a patient in need of such treatment. This method also includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention involves a method for regression of atherosclerosis, including regression of atherosclerotic plaques existing at the time the instant treatment is begun, comprising administering a therapeutically effective amount a compound of Formula I to a patient in need of such treatment.

Another aspect of this invention involves a method for preventing or reducing the risk of atherosclerotic plaque rupture comprising administering a prophylactically effective amount of a compound of Formula I to a patient in need of such treatment.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of leukotriene biosynthesis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-inflammatory, anti-allergic or anti-atherosclerotic use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, anti-atherosclerotic or anti-allergic use is from about 0.001 mg to about 25 mg (preferably from 0.01 mg to about 1 mg) of a compound of Formula I per kg of body weight per day and for cytoprotective use from 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory, anti-allergic or anti-atherosclerotic use is, e.g., from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The pharmaceutical compositions of the present invention comprise a compound of Formula I as an active ingredient and a pharmaceutically acceptable carrier and optionally other therapeutic ingredients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of Formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |

| -continued | |
|---|---|
| Tablet | mg/tablet |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

A therapeutically effective amount of a compound of Formula I can be used for the preparation of a medicament useful for treating or preventing any of the medical conditions described herein, in dosage amounts described herein. For example, a compound of Formula I can be used for the preparation of a medicament useful for the treatment of asthma, allergies and allergic conditions, inflammation, COPD or erosive gastritis. Additionally, the medicament may be useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. The medicament comprised of a compound of Formula I may also be prepared with one or more additional active agents, such as those described below.

One or more additional active agents may be used in combination with the compounds of Formula I of this invention in a single dosage formulation, or the active agents of the combination may be administered to the patient in separate dosage formulations, which allows for concurrent or sequential administration of the active agents.

In addition to the compounds of Formula I, the pharmaceutical compositions of the present invention can also contain other active agents (i.e., ingredients), such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:

(1) propionic acid derivatives;
(2) acetic acid derivatives;
(3) fenamic acid derivatives;
(4) oxicams; and
(5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g., —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

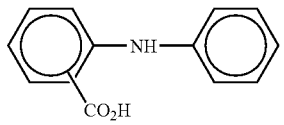

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenyl-carboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

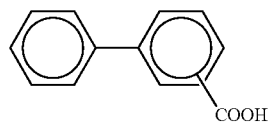

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

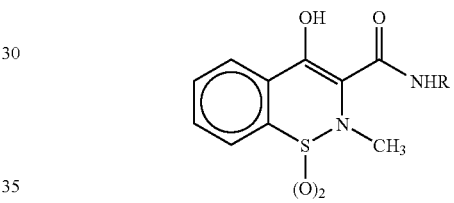

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetanine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used:

480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI- 901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 Dec. 2, 1981), benadryl, cimetidine, famotidine, fraine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126-131 (1985), and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc., and the corticosteroids, hydrocortisone, methylprednisolone, betamethasone, dexamethasone, beclomethasone, and the like.

Furthermore, additional active agents such as anti-atherosclerotic agents may be used in combination with the compounds of Formula I of this invention. The additional active agent or agents can be lipid altering compounds such as HMG-CoA reductase inhibitors, or agents having other pharmaceutical activities, or agents that have both lipid-altering effects and other pharmaceutical activities. Examples of HMG-CoA reductase inhibitors useful for this purpose include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin particularly the sodium salt thereof (see U.S. Pat. No. 5,354,772); atorvastatin, particularly the calcium salt thereof (see U.S. Pat. No. 5,273,995); nisvastatin also referred to as NK-104 (see PCT international publication number WO 97/23200); and rosuvastatin (also known as ZD-4522, see U.S. Pat. No. 5,260,440). Additional active agents which may be employed in combination with a a compound of Formula I include but are not limited to HMG-CoA synthase inhibitors; cholesterol absorption inhibitors such as ezetimibe which is 1-(4-fluorophenyl)-3(R)-[3(S)-(4-fluorophenyl)-3-hydroxypropyl)]4(S)-(4-hydroxyphenyl)-2-azetidinone, described in U.S. Pat. Nos. Re. 37721 and 5,846,966; cholesterol ester transfer protein (CETP) inhibitors, for example JTT-705 and CP529,414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl)phenyl]methyl]-benzamide, known as KRP-297; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

Compounds of Formula I can be tested using the following assays to determine their mammalian leukotriene biosynthesis inhibiting activity. Representative tested compounds of Formula I were shown to be inhibitors of leukotriene biosynthesis, each having an $IC_{50}$ less than or equal to 500 nM in the Human Polymorphonuclear Leukocyte $LTB_4$ assay, described below. The representative tested compounds were also shown to have activity as 5-LO inhibitors in either or both of the Human 5-Lipoxygenase Enzyme Assay and the 5-Lipoxygenase Human Whole Blood Assay, both described below.

Human Polymorphonuclear (PMN) Leukocyte $LTB_4$ Assay

Human blood was obtained by venepuncture from consenting volunteers who have not taken medication within the previous 7 days. The blood was immediately added to 10% (v/v) trisodium citrate (0.13M). PMNs were isolated from the anticoagulated blood by dextran sedimentation of erythrocytes followed by centrifugation through Histopaque-1077 (Sigma). Contaminating erythrocytes were removed by hypotonic lysis. PMNs were resuspended at $2.5×10^5$/ml in HEPES (15 mM)-buffered Hanks balanced salt solution containing Ca$^{2+}$ (1.4 mM) and Mg$^{2+}$ (0.7 mM), pH 7.4.

PMNs (0.5 ml; 1.25×10$^5$ cells) were placed in 1.2 ml plastic tubes (Marsch Biomedical Products) and incubated (37° C., 2 min) with 2 μl of test compounds at the desired concentration or vehicle (DMSO) as control. The synthesis of LTB$_4$ was initiated by the addition of calcium ionophore. A23187 (Sigma, final concentration 10 μM) or vehicle in control samples and allowed to proceed for 5 minutes at 37° C. The reactions were terminated with the addition of cold methanol (0.25 ml).

Samples were diluted 4-fold in Assay Designs' assay buffer provided in their LTB$_4$ Enzyme Immunoassay kit. Quantitation of the LTB4 content was performed as per manufacturer's protocol. Inhibitory dose-response curves were constructed using a four-parameter algorithm and from these the IC$_{50}$ values were determined.

Human 5-Lipooxygenase Enzyme Assay

The activity of 5-lipoxygenase was measured using a spectrophotometric assay and recombinant human 5-lipoxygenase as a source of enzyme. Human 5-lipoxygenase was purified from Sf9 cells infected with the recombinant baculovirus rvH5LO (8-1) containing the coding sequence for human 5-lipoxygenase as described by Percival et al., (Eur. J. Biochem 210, 109-117, 1992). The enzymatic activity was measured using a spectrophotometric assay from the optimal rate of conjugated diene formation (absorbance at 238 nm) using the procedure described in Riendeau et al. (Biochem. Pharmacol. 38, 2313-2321, 1989) with minor modifications. The incubation mixture contained 25 mM potassium phosphate, pH 7.5, 0.1 mM EDTA, 0.3 mM CaCl$_2$, 24 μg/ml phosphatidylcholine, 0.1 mM ATP, 0.5 mM DTT, 20 μM arachidonic acid (2 μl from a 100-fold solution in ethanol), inhibitor (2 μl aliquot from a 100-fold solution in DMSO) and an aliquot of purified 5-lipoxygenase. Reactions were initiated by the addition of the purified 5-lipoxygenase and the rate of conjugated diene production was followed for 5 minutes at room temperature. The reaction was performed in a Costar UV plate (Cat. #3635) and the absorbance changes at 238 nm were recorded with a Molecular Devices UV/VIS 96 well spectrophotometer (Spectra Max 190) using SOFTmax PRO software. Enzymatic activity was calculated from the optimal rate of the reaction by a linear fit of the increase in absorbance at 238 nm over 36 seconds. When the rate of diene formation is low (<0.01 Absorbance Unit/min) the linear fit is performed over 180 seconds. The results are expressed as percentage of inhibition of the reaction rate relative to controls (typically between 0.001-0.005 Absorbance Unit/min) containing the DMSO vehicle.

5-Lipooxygenase Human Whole Blood Assay

Fresh blood was collected in heparinized tubes by venipuncture from consenting volunteers. These volunteers have no apparent inflammatory conditions and have not taken any nonsteroidal anti-inflammatory drugs for at least 4 days prior to blood collection. Plasma was separated from the blood of each individual volunteer by centrifuging approximately 10 mls of blood. A 50 mM stock solution of the calcium ionophore A23187 (Sigma, St Louis, Mo., USA) in DMSO was diluted 20 fold with each volunteer's plasma to obtain a 2.5 mM working solution. A 500 μl aliquot of each blood was pre-incubated with either 1 μl of vehicle (DMSO) or test compounds in DMSO at 37° C. for 15 minutes. This was followed with the addition of 5 μl of either plasma or the 2.5 mM working solution (for each experiment, the blood and plasma was from the same volunteer) resulting in a final concentration of 25 μM of A23187. The blood mixture was incubated at 37° C. for 30 minutes then centrifuged at 1500 g at 4° C. for 10 minutes. The supernatant plasma was collected from all samples and stored at 4° C. All supernatant plasma samples were tested for the production of leukotriene B$_4$ (LTB$_4$) using the LTB$_4$ enzyme immunosorbent assay (EIA) kit from Assay Designs (Ann Arbor, Mich., USA) according to the manufacturer's instructions.

Compounds of Formula I of this invention can be prepared according to the following methods and Examples below. Some abbreviations used herein include: Bu=butyl; DAST=diethylaminosulfur trifluoride; DBU=1,8-diazabicyclo[5.4.0]undec-7-ene; DME=ethylene glycol dimethyl ether; DMF=N,N-diethylformamide; DMSO=dimethyl sulfoxide; EtOH=ethanol; Et$_2$O=diethyl ether; Et$_3$N=triethylamine; EtOAc=ethyl acetate; h=hours; HOAc=acetic acid; KHMDS=potassium bis(trimethylsilyl)amide; LDA=lithium diisopropylamide; m-CPBA=3-chloroperoxybenzoic acid; MeOH=methanol; NMP=1-methyl-2-pyrrolidinone; OTf=trifluoromethanesulfonate=triflate; O-THF=O-tetrahydropyran-2-yl; rt=room temperature; TFA=trifluoro acetic acid; THF=tetrahydrofuran.

7-Bromo-4-trifluoromethanesulfonyloxycoumarin (structure v-a) can be prepared as shown in Scheme 1 below. Description of how to make v-a is also found in the procedures described in U.S. Pat. No. 5,552,437 in Scheme 1 at columns 17-18 (see structure V) therein and in the section titled "Preparation Of Coumarins" starting at column 58 therein. Bromophenol ii can be acetylated by treating a mixture of ii and acetyl chloride in the presence of a base such as pyridine in a solvent such as dichloromethane to yield the corresponding acetate which, upon heating neat with a Lewis acid such as aluminum chloride, gives the acyl derivative iii. Reaction of iii with first an inorganic base such as sodium hydride in an organic solvent such as benzene followed by addition of a carbonate such as diethylcarbonate furnishes the intermediate iv. The intermediate iv is then transformed using trifluoromethanesulfonic anhydride, in the presence of an amine such as triethylamine, in a neutral solvent such as dichloromethane, to the corresponding triflate v-a.

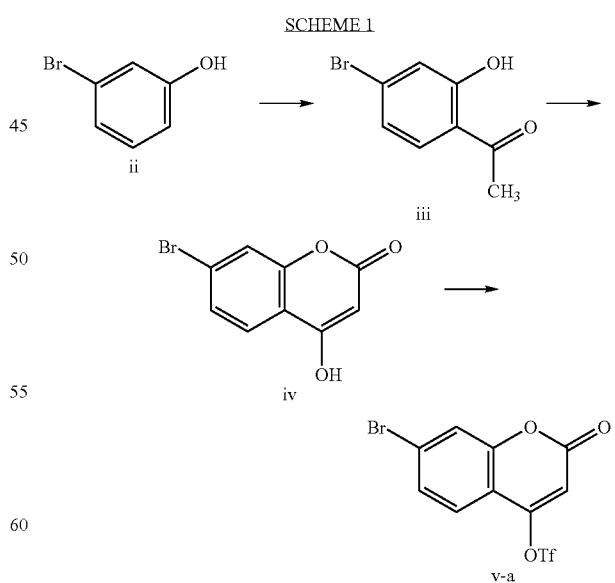

SCHEME 1

The bromo-4-trifluoromethanesulfonyloxycoumarin of structure v-b can also be prepared following the procedures described above for preparing v.

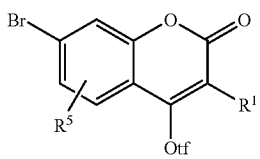

As shown in Scheme 2, triflate v-b can also be prepared by acylation of bromophenol (substituted or not) with AlCl$_3$ and an acyl chloride followed by rearrangement upon heating in dichloroethane. Treatment with a carbonate such as ethyl carbonate and a hydride such as NaH in toluene yields triflate v-b after conversion of the phenol.

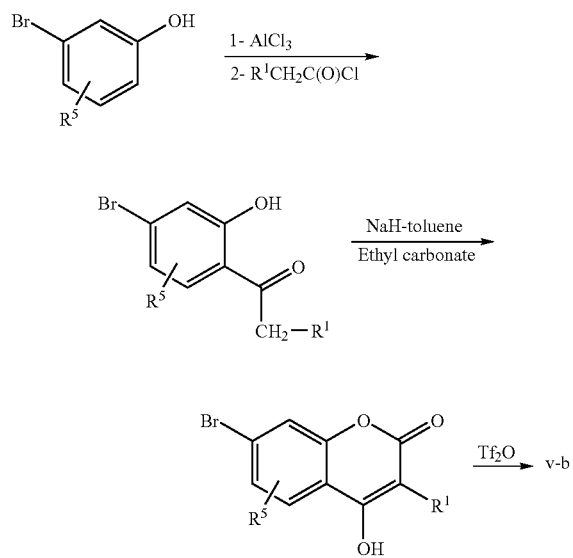

The following structural formulas III, IIIa and IIIb are referred to in the following schemes:

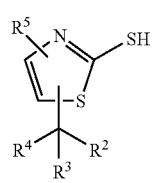

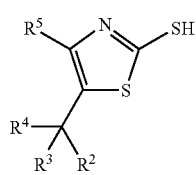

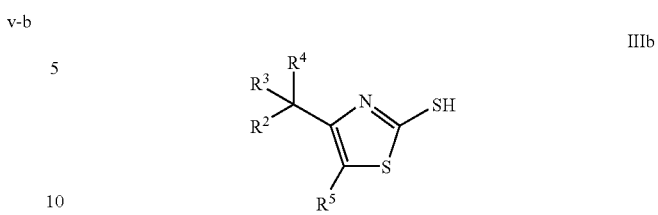

Compounds of Formula I of the present invention may be prepared employing general synthetic procedures known in the art, including the methods described below and the methods described in U.S. Pat. No. 5,552,437, which is herein incorporated by reference. The synthetic routes outlined in Schemes A to E are provided for illustrative purposes. In the Schemes and the description of the Schemes, the term "Ar" is equivalent to "A" as defined in Formula I.

METHOD A: Boronic acids and esters can be prepared from the corresponding halide according to literature procedures and references cited therein (Charette, A. B., Giroux, A. J., Org. Chem. 1996, 61, 8718; Ishiyama, T., Murata, M., Miyaura, N. J., Org. Chem. 1995, 60, 7508; Miyaura, N., Suzuki, A., Chem. Rev, 1995, 95, 2457; Murata, M., Watanabe, S., Masuda, Y. J., Org. Chem. 1997, 62, 6458; Watanabe, T., Miyaura, N., Suzuki, A., Synlett, 1992, 207; Maddaford, S., Keay, B. A., J. Org. Chem. 1994, 59, 6501; Cristofoli, W. A., Keay, B. A., Tetrahedron Lett. 1991, 32, 5881; Passafaro, M. S., Keay, B. A., Tetrahedron Lett. 1996, 37, 429; Serafin, B., Makosza, M., Tetrahedron, 1963, 19, 821). In some cases, the triflate, the tin or the zinc derivatives may be used instead of the boronic acid.

As shown in Scheme A, triflate v-b (U.S. Pat. No. 5,552,437) was treated with the appropriate boronic acid or ester, a catalyst such as tetrakis(triphenylphosphine) palladium and cesium fluoride or Na$_2$CO$_3$ or a base in an inert solvent such as DME at 80-90° C. to yield coumarin II.

The coupled product II is treated with thiol III and an inorganic base such as K$_2$CO$_3$ in DMF or NMP between 80-120° C. to afford compound IV. Alternatively, the thiol III can be treated with KOH in methanol for a few minutes and the solvent is removed to dryness. Coumarin II and the solvent are added and the mixture is heated to 80-120° C. to yield IV.

At any point of the synthesis, if R$^2$=OH, it can be treated with TFA/Et$_3$SiH to obtain deoxygenated product V. Deoxygenation is also accomplished from a radical reaction done on the corresponding xanthogene.

At any point of the synthesis, if R$^2$=OH, it can be reacted with alkyl halides with a base such as K$_2$CO$_3$ or a hydride or an organic base such as DBU to give ether adducts. It can also be acylated with anhydrides or acyl chlorides. Treatment by a mineral or organic acid on an appropriate substrate gives the elimination product alkene. These transformations can be applied to any method if there is one OH group that can be eliminated.

At any point of the synthesis, if R$^2$=OH, treatment with DAST in CH$_2$CL$_2$ at −78° C. and slowly increasing the temperature of the reaction mixture to 0° C. gives the corresponding fluoride compound after work-up. In compounds v-b and II, Br can be replaced by F, Cl or I.

At any point in the preparation of a sulfide, the sulfoxide or sulfone can be prepared with hydrogen peroxide, m-CPBA or the like.

SCHEME A

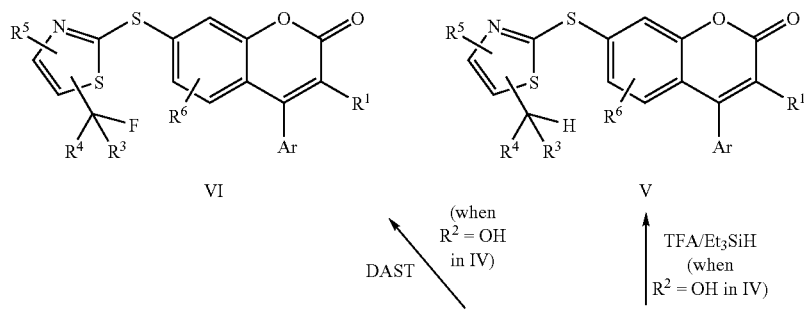

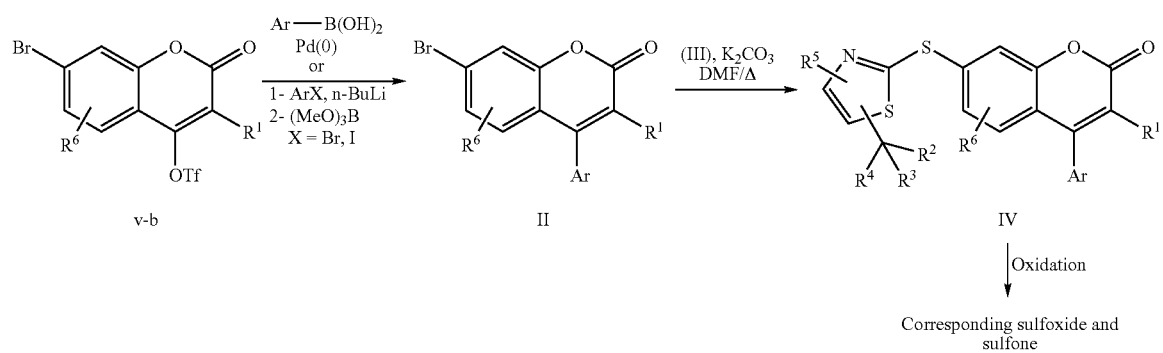

METHOD B: As shown in Scheme B, to a suspension of AlCl$_3$ in a chlorinated solvent such as dichloroethane is added the desired acyl chloride at room temperature. 3-Bromoanisole (substituted or not) in the same solvent is added dropwise. At the end of the reaction the mixture is poured into acidic water. After purification on silica gel, the solid is treated with pyridine hydrochloride at 120 to 170° C. or BBr$_3$ in CH$_2$Cl$_2$ to remove the methoxy group. After work-up, compound IX is obtained. Alternatively, 3-bromoanisole can be replaced by 3-bromophenol. Treatment of 3-bromophenol and AlCl$_3$ with the acyl chloride followed by heating in a chlorinated solvent affords IX.

Compound X is prepared by the addition of phosphorous oxychloride to an N,N-dialkylamide in a high boiling solvent such as dichlorobenzene at room temperature. After 30 minute, IX is added and 10 minute later, the mixture is heated to 1400 C for the appropriate amount of time. Alternatively, IX can be treated with a triphenylphosphoranylidene at 100-140° C. in a high boiling solvent such as toluene and xylene to afford compound X. The phenol IX can also be acylated in pyridine or in an inert solvent with a base to XII and treated with a base such as KHMDS at 0° C. to furnish X. Following method A with X and compound III, compound XI is obtained.

If Ar is a pyridine it can be converted to a pyridone via the preparation of the N-oxide followed by treatment with acetic anhydride and heating in basic conditions.

SCHEME B

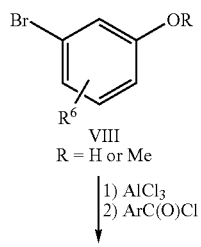

VIII
R = H or Me

1) AlCl$_3$
2) ArC(O)Cl

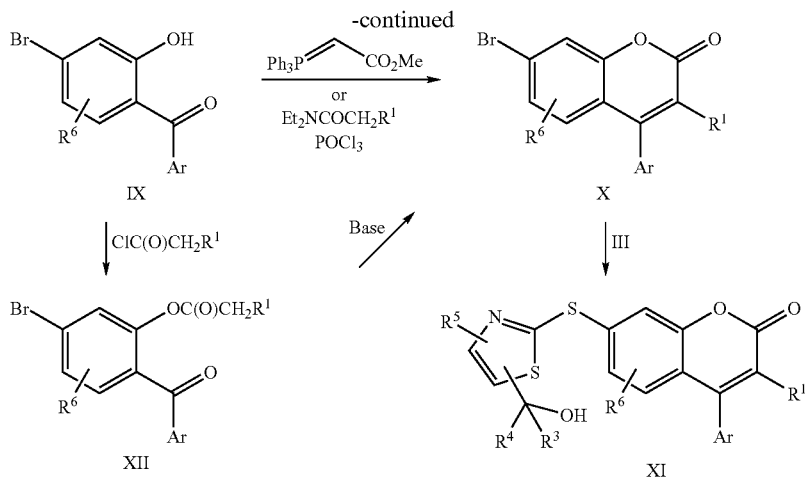

METHOD C: As shown in Scheme C, thiazole XIII is treated with a strong base such as BuLi or LDA in an inert solvent such as THF or Et$_2$O at -78° C. followed by the addition of a carbonyl derivatives to furnish III. Alternatively, the bis-anion formed by treatment of XIII with LDA at -78° C. is treated with an anhydride, an ester or an acyl chloride to give ketone XIV. To ketone XIV is added a commercially available Grignard reagent or one that is prepared from a suitably protected (such as O-THF, dioxolane, etc.) aliphatic chain having a bromo or an iodo atom at the end of the chain. The protected group used can be found in "Protective groups in organic synthesis", Greene, T. W.; Wuts, P. G. M.; 1999, third edition, Wiley and Sons. Once the protecting group is removed, other functionalities are introduced such as nitrile, ether, carboxylic acid, ester and sulfide.

Treatment of ester or nitrile (CH$_3$—X$^2$) with a base such as LDA in an inert solvent such as THF or Et$_2$O at -78° C. followed by addition of XIV also furnished III.

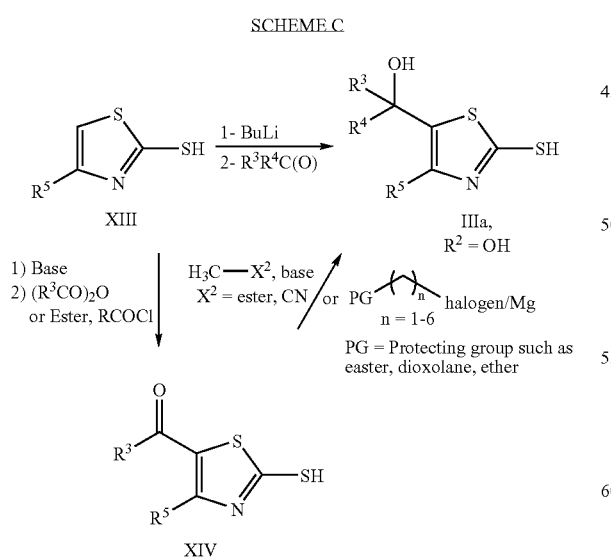

METHOD D: As depicted in Scheme D, tetrazole derivatives are prepared from the alcohol III or IV according to Fortin, R.; Brochu, C. Tetrahedron Lett. 1994, 35, (52) 9681. To the tertiary alcohol IV in acetonitrile at rt was added 5 equivalent of 1H-tetrazole and 40% of a Lewis acid such as zinc triflate. The reaction mixture was left overnight. After quenching with NH$_4$OAc and removal of the solvent, the crude product was purified on silica gel with 2/8 toluene:EA to 100% EA.

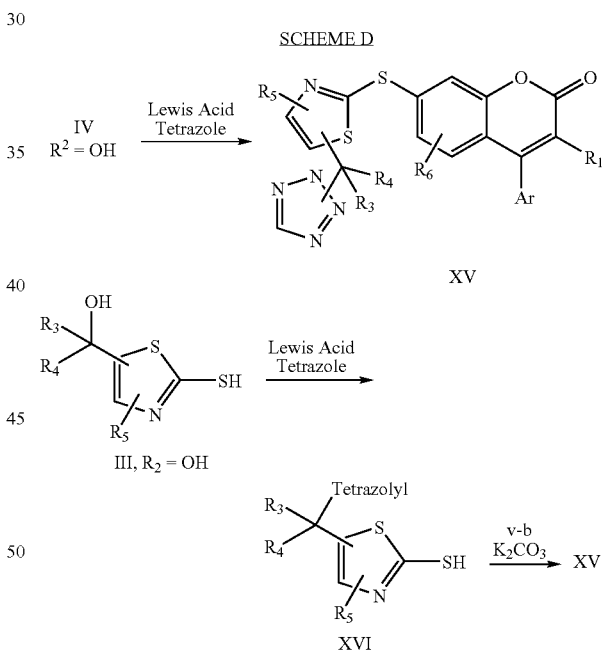

METHOD E: As shown in Scheme E, thiazole XVI is prepared according to D'Amico and Bartram (J. Org. Chem. 1960, 25, 1336 and references cited therein). Grignard's reagent (or lithiated reagent) is added at low temperature to yield IIIb. An intermediate ketone is usually formed when a Grignard reagent is used. This ketone can be used to add a different Grignard reagent. Alternatively, XVII is halogenated with bromine in MeOH or HOAc (rt to 80° C.) or any other methods that can add a Cl or a Br alpha to a ketone to yield XVII. It is then treated with ammonium dithiocarbamate in ethanol to yield IIIb.

SCHEME E

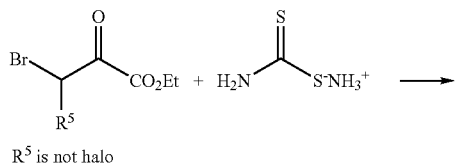

$R^5$ is not halo

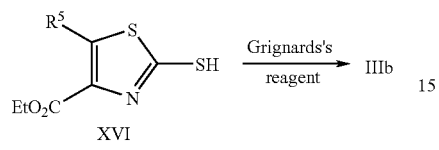

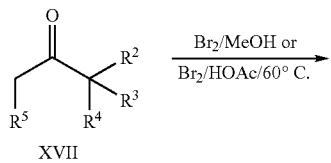

XVII

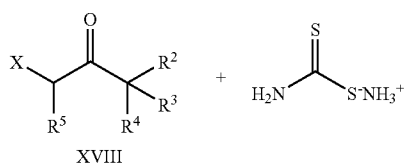

XVIII $R^5$ is not halo
X = Cl, Br

EXAMPLE 1

4-(4-fluorophenyl)-7-({5-[1-hydroxy-1-(trifluoromethyl)propyl]-1,3-thiazol-2-yl}thio)-2H-chromen-2-one Step 1:
7-bromo-4-(4-fluorophenyl)-2H-chromen-2-one

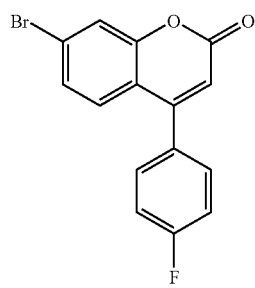

To a solution of triflate (compound V of scheme 1, in U.S. Pat. No. 5,552,437) (3.0 g, 8.0 mmol) in 27 ml of THF was added 4-fluorophenyl boronic acid (1.2 g, 8.8 mmol), (Ph₃P)₄Pd (465 mg, 0.4 mmol) and aqueous Na₂CO₃ (8.8 ml, 17.7 mmol). The mixture was heated at 50° C. for 2 h, cooled and partitioned between aqueous NH₄Cl and EtOAc. The layers were separated and the aqueous phase was extracted with EtOAc. The combined organic layers were dried over anhydrous MgSO₄. The solvent was evaporated and the residue chromatographed on silica gel (toluene:EtOAc; 9:1) to give the title compound.

Step 2: 1,1,1-trifluoro-2-2-mercapto-1,3-thiazol-5-yl)butan-2-ol

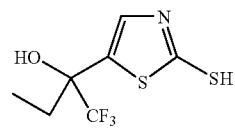

To a solution of diisopropylamine (4.32 g, 42.6 mmol) in 50 ml of THF at –78° C. was added BuLi (1.6 M in hexanes, 26.6 ml, 42.6 mmol). After 15 min, a solution of 2-mercaptothiazole (2.0 g, 17.0 mmol) in 10 ml of THF was added dropwise. After 5 min, 1,1,1-trifluoro-2-butanone (1.07 g, 8.5 mmol) was added. The mixture was stirred 3 h at –78° C. and partitioned between aqueous NH₄Cl and EtOAc. The layers were separated and the aqueous phase was extracted with EtOAc. The combined organic layers were dried over anhydrous MgSO₄. The solvent was evaporated and the residue chromatographed on silica gel (hexanes: EtOAc;1:1) to give the title compound.

Step 3: 4-4-fluorophenyl)-7-({5-[1-hydroxy-1-trifluoromethyl)propyl]-1,3-thiazol-2-yl}thio)-2H-chromen-2-one

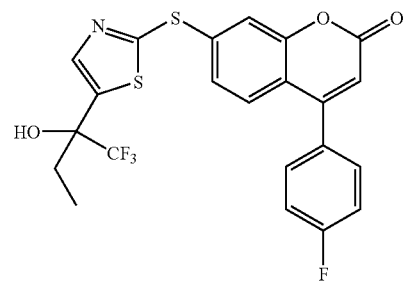

A solution of 7-bromo-4-(4-fluorophenyl)-2H-chromen-2-one (829 mg, 2.6 mmol), the thiol 1,1,1-trifluoro-2-(2-mercapto-1,3-thiazol-5-yl)butan-2-ol (632 mg, 2.6 mmol) and potassium carbonate (1.08 g, 7.8 mmol) in 17 ml of 1-methyl-2-pyrrolidinone (NMP) was heated at 120° C. overnight. The mixture was cooled to room temperature and partitioned between aqueous NH₄Cl and EtOAc. The layers were separated and the aqueous phase was extracted with EtOAc. The combined organic layers were washed with water, brine and dried over anhydrous MgSO₄. The solvent was evaporated and the residue chromatographed on silica gel (toluene: acetone; 95:5) to give the title compound. $^1$H NMR (400 MHz, CDCl₃): δ 7.76 (s, 1H), 7.56 (d, 1H), 7.44-7.48 (m, 3H), 7.36 (dd, 1H), 7.25 (m, 2H), 6.39 (s, 1H), 2.93 (br s, 1H), 2.12 (q, 2H), 0.97 (t, 3H).

EXAMPLE 2

4-(4-fluorophenyl)-7-{[5-(1-hydroxycyclopentyl)-1,3-thiazol-2-yl]thio}-2H-chromen-2-one Step 1: 1-(2-mercapto-1,3-thiazol-5-yl)cyclopentanol

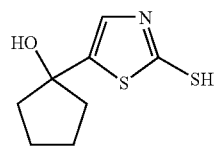

Following the procedure described in Example 1, Step 2, for the thiol 1,1,1-trifluoro-2-(2-mercapto-1,3-thiazol-5-yl)butan-2-ol but substituting the 1,1,1-trifluoro-2-butanone with cyclopentanone, the title compound was obtained.

Step 2: 4-(4-fluorophenyl)-7-{[5-(1-hydroxycyclopentyl)-1,3-thiazol-2-yl]thio}-2H-chromen-2-one

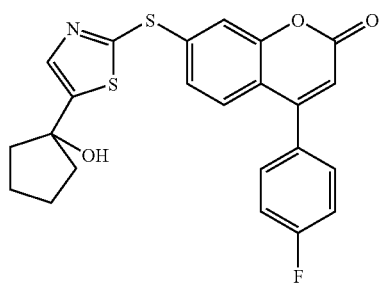

Following the procedure described in Example 1, Step 3, for 4-(4-fluorophenyl)-7-({5-[1-hydroxy-1-trifluoromethyl)propyl]-1,3-thiazol-2-yl}thio)-2H-chromen-2-one but substituting the thiol therein with 1-(2-mercapto-1,3-thiazol-5-yl)cyclopentanol, the title compound was obtained. $^1$H NMR (400 MHz, acetone-$d_6$): δ 7.78 (s, 1H), 7.66 (m, 2H), 7.52 (d, 1H), 7.45 (d, 1H), 7.37-7.41 (m, 3H), 6.39 (s, 1H), 4.69 (s, 1H), 1.90-2.10 (m, 6H), 1.80-1.84 (m, 2H).

EXAMPLE 3

4-(4-fluorophenyl)-7-({5-[2,2,2-trifluoro-1-hydroxy-1-(trifluoromethyl)ethyl]-1,3-thiazol-2-yl}thio)-2H-chromen-2-one Step 1: 1,1,1,3,3,3-hexafluoro-2-(2-mercapto-1,3-thiazol-5-yl)propan-2-ol

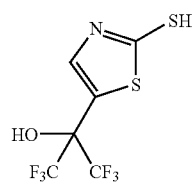

Following the procedure described in Example 1, Step 2, for the thiol 1,1,1-trifluoro-2-(2-mercapto-1,3-thiazol-5-yl)butan-2-ol but substituting the 1,1,1-trifluoro-2-butanone with hexafluoroacetone, the title compound was obtained. Since hexafluoroacetone is a gas, it was bubbled in the solution.

Step 2: 4-(4-fluorophenyl)-7-({5-[2,2,2-trifluoro-1-hydroxy-1-(trifluoromethyl)ethyl]-1,3-thiazol-2-yl}thio)-2H-chromen-2-one

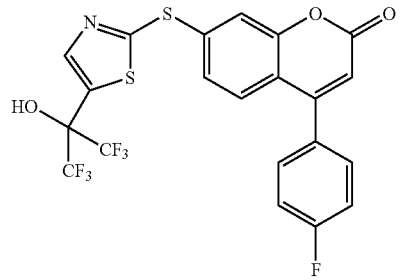

Following the procedure described in Example 1, Step 3, for 4-(4-fluorophenyl)-7-({5-[1-hydroxy-1-(trifluoromethyl)propyl]-1,3-thiazol-2-yl}thio)-2H-chromen-2-one but substituting the thiol therein with 1,1,1,3,3,3-hexafluoro-2-(2-mercapto-1,3-thiazol-5-yl)propan-2-ol, the title compound was obtained. $^1$H NMR (400 MHz, acetone-$d_6$): δ 8.26 (s, 1H), 8.06 (s, 1H), 7.74 (d, 1H), 7.57-7.70 (m, 4H), 7.40 (t, 2H), 6.47 (s, 1H).

EXAMPLE 4

7-{[5-(1-ethylpropyl)-1,3-thiazol-2-yl]thio}-4-(4-fluorophenol)-2H-chromen-2-one Step 1: 3-(2-mercapto-1,3-thiazol-5-yl)pentan-3-ol

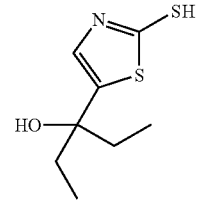

Following the procedure described in Example 1, Step 2, for the thiol 1,1,1-trifluoro-2-(2-mercapto-1,3-thiazol-5-yl)butan-2-ol but substituting the 1,1,1-trifluoro-2-butanone with 3-pentanone, the title compound was obtained.

Step 2: 5-(1-ethylpropyl)-1,3-thiazole-2-thiol

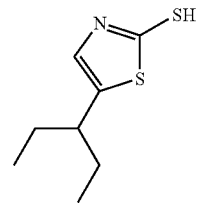

To a solution of 3-(2-mercapto-1,3-thiazol-5-yl)pentan-3-ol (515 mg, 2.5 mmol) in 30 ml of $CH_2Cl_2$ at 0° C. was added triethylsilane (2.0 ml, 12.5 mmol) and TFA (2.0 ml, 25.9 mmol). The mixture was stirred for 1 h at 0° C. then warmed to room temperature. After 1 h, the reaction mixture was diluted with EtOAc and quenched with a saturated solution of sodium bicarbonate. The layers were separated and the aqueous phase was extracted with EtOAc. The combined organic layers were washed with brine, dried over anhydrous MgSO₄ and the solvent evaporated. The crude compound showed a mixture of alkene and desired product. The crude mixture was then resubmitted to the same reaction condition to get complete conversion. The crude was chromatographed on silica gel (hexane:EtOAc; 95:5 to 80:20) to the title compound.

Step 3: 7-{[5-(1-ethylpropyl)-1,3-thiazol-2-yl]thio}-4-(4-fluorophenyl)-2H-chromen-2-one

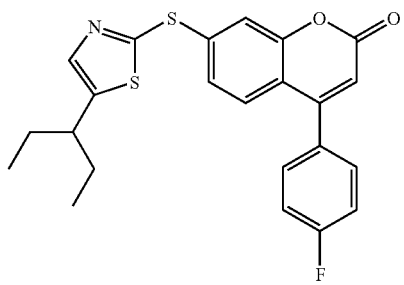

Following the procedure described in Example 1, Step 3, for 4-(4-fluorophenyl)-7-({5-[1-hydroxy-1-(trifluoromethyl)propyl]-1,3-thiazol-2-yl}thio)-2H-chromen-2-one but substituting the thiol therein with 5-(1-ethylpropyl)-1,3-thiazole-2-thiol, the title compound was obtained. ¹H NMR (400 MHz, acetone-d₆): δ 7.64-7.69 (m, 3H), 7.51 (d, 1H), 7.45 (d, 1H), 7.34-7.40 (m, 3H), 6.38 (s, 1H), 2.84 (m, 1H), 1.78 (m, 2H), 1.56 (m, 2H), 0.87 (t, 6H).

EXAMPLE 5

Alternate preparation for 7-{[5-(1-ethylpropyl)-1,3-thiazol-2-yl]thio}-4-(4-fluorophenyl)-2H-chromen-2-one Step 1: 7-{[5-(1-ethyl-1-hydroxypropyl)-1,3-thiazol-2-yl]thio}-4-(4-fluorophenyl)-2H-chromen-2-one

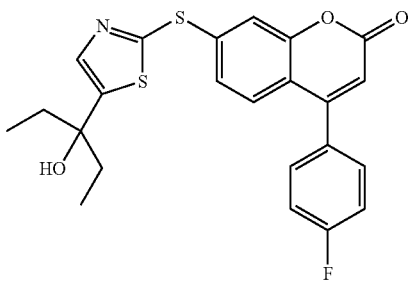

Following the procedure described in Example 1, Step 3, for making 4-(4-fluorophenyl)-7-({5-[1-hydroxy-1-(trifluoromethyl)propyl]-1,3-thiazol-2-yl}thio)-2H-chromen-2-one but substituting the thiol therein with 3-(2-mercapto-1,3-thiazol-5-yl)pentan-3-ol (made in step 1 of Example 4), the title compound was obtained.

¹H NMR (400 MHz, acetone-d₆): δ 7.70 (s, 1H), 7.64-7.67 (m, 2H), 7.50 (d, 1H), 7.35-7.42 (m, 4H), 6.38 (s, 1H), 4.45 (s, 1H), 1.88 (q, 4H), 0.88 (t, 6H).

Step 2: 7-{[5-(1-ethylpropyl)-1,3-thiazol-2-yl]thio}-4-(4-fluorophenyl)-2H-chromen-2-one

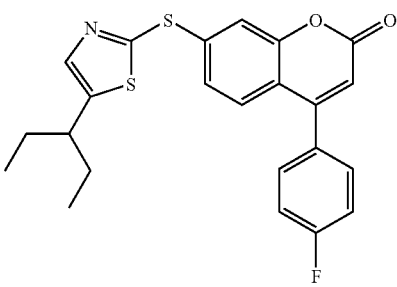

To a solution of 7-{[5-(1-ethyl-1-hydroxypropyl)-1,3-thiazol-2-yl]thio}-4-(4-fluorophenyl)-2H-chromen-2-one (26 mg, 0.06 mmol) in 1 mL of CH₂Cl₂ at 0° C. was added triethylsilane (100 μL) and TFA (100 μL). The mixture was stirred for 1 h at 0° C. then warmed to room temperature with more triethylsilane (250 μL). The solvent was removed in vacuo and chromatographed on silica gel (hexane:EtOAc; 90:10 to 80:20) to yield the title compound.

EXAMPLE 6

4-(4-Fluorophenyl)-3-methyl-7-({5-[2,2,2-trifluoro-1-hydroxy-1-(trifluoromethyl)ethyl]-1,3-thiazol-2-yl}thio)-2H-chromen-2-one Step 1:
(4-Bromo-2-methoxyphenyl)(4-fluorophenyl)methanone

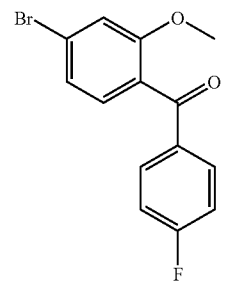

To a suspension of AlCl₃ (14.7 g, 110 mmol) in 250 mL of 1,2-dichloroethane was added 4-fluorobenzoyl chloride (11.8 mL, 100 mmol) at rt. The resulting mixture was stirred at rt for 15 min. and 3-bromoanisole (16.8 g, 90.0 mmol) in 20 mL of 1,2-dichloroethane was added. After 1 h at rt, the brown solution was poured into ice. 2N HCl was added to the aqueous layer followed by an extraction with CH₂Cl₂. The combined organics were dried (MgSO₄), filtered and concentrated. The residue was subjected to chromatography on silica gel (EtOAc/hexane 5:95 to 7:93) affording 5.1 g of a solid that was triturated with 20 mL of EtOAc/hexane (10:90). The title compound was obtained from filtration, and additional product was recovered from the mother liquors.

Step 2: (4-Bromo-2-hydroxyphenyl)(4-fluorophenyl)methanone

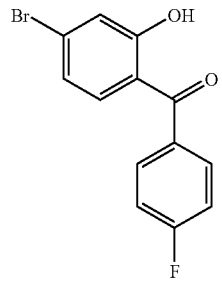

A mixture of (4-bromo-2-methoxyphenyl)(4-fluorophenyl)methanone (1.60 g, 5.18 mmol) and pyridine hydrochloride (15.0 g, 130 mmol) was heated at 170° C. for 4.5 h and allowed to cool to rt. The resulting mixture was diluted with Et$_2$O and washed with a 2N HCl solution. The ether layer was extracted twice with a 1N NaOH solution. The combined aqueous layers were acidified and extracted with Et$_2$O, and the combined organics dried (MgSO$_4$), filtered and concentrated. The title compound was obtained as a yellow solid, slightly contaminated with an impurity. It was used as such in the following step.

Step 3: 7-Bromo-4-(4-fluorophenyl)-3-methyl-2H-chromen-2-one

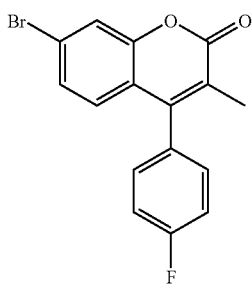

Phosphorous oxychloride (95.0 µL, 1.02 mmol) was added dropwise, at rt to a solution of N,N-diethylpropionamide (146 µL, 1.02 mmol) in 1,2-dichlorobenzene (1 mL). After 30 min. at rt, (4-bromo-2-hydroxyphenyl)(4-fluorophenyl)methanone (300 mg, 1.02 mmol) was added all at once. After 10 min. the reaction mixture was heated at 140° C. for 16 h and allowed to cool to rt. It was poured into 5% NaHCO$_3$ (20 mL) and the resulting mixture stirred at 60° C. for 20 min., cooled to rt, acidified (pH=1) with 6N HCl and extracted with CHCl$_3$. The combined organics were washed with water and brine, dried (Na$_2$SO$_4$), filtered and concentrated. The residue was subjected to chromatography on silica gel (EtOAc/toluene 1:100) affording the title compound as a white solid, contaminated with ~10% of an impurity. It was used as such in the following step.

Step 4: 4-(4-Fluorophenyl)-3-methyl-7-({5-[2,2,2-trifluoro-1-hydroxy-1-(trifluoromethyl)ethyl]-1,3-thiazol-2-yl}thio)-2H-chromen-2-one

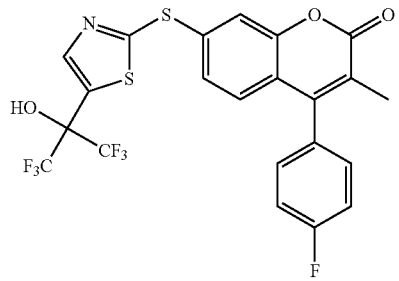

Following the procedure described in Example 1, Step 3, for 4-(4-fluorophenyl)-7-({5-[1-hydroxy-1-trifluoromethyl)propyl]-1,3-thiazol-2-yl}thio)-2H-chromen-2-one but substituting the thiol therein with 1,1,1,3,3,3-hexafluoro-2-(2-mercapto-1,3-thiazol-5-yl)propan-2-ol and the aryl bromide therein with 7-bromo-4-(4-fluorophenyl)-3-methyl-2H-chromen-2-one, the title compound was obtained.

$^1$H NMR (500 MHz, acetone-d$_6$): δ 8.24 (s, 1H), 8.02 (s, 1H), 7.74 (d, 1H), 7.47-7.54 (m, 3H), 7.41-7.44 (m, 2H), 7.15 (d, 1H), 1.98 (s, 3H).

EXAMPLE 7

(+)-(S) and (−)-(R)-4-(4-Fluorophenyl)-7-({5-[1-hydroxy-1-(trifluoromethyl)propyl]-1,3-thiazol-2-yl}thio)-2H chromen-2-one Step 1: Separation on chiral HPLC column of both enantiomers of 1,1,1-trifluoro-2-(2-mercapto-1,3-thiazol-5-yl)butan-2-ol

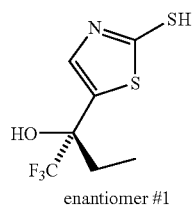
enantiomer #1

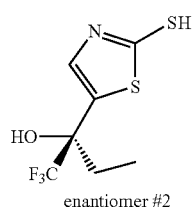
enantiomer #2

A solution of (±)-1,1,1-trifluoro-2-(2-mercapto-1,3-thiazol-5-yl)butan-2-ol (1.2 g) from step 2 of example 1 in EtOH/hexane (20 ml, 1:4) was injected (1×1.2 g) onto a CHIRAL-PAK AD preparative (5 cm×50 cm) HPLC column (eluting with hexane/EtOH, 4:1; at 75 ml/min with UV detection at 280 nm). The enantiomers were separated with the faster eluting enantiomer having a retention time of ~19 min (enantiomer #1, (2S)-1,1,1-trifluoro-2-(2-mercapto-1,3-thiazol-5-yl)butan-2-ol) and the slower eluting enantiomer having a retention time of ~34 min (enantiomer #2, (2R)-1,1,1-trifluoro-2-2-mercapto-1,3-thiazol-5-yl)butan-2-ol). The eluants were concentrated to provide enantiomer #1 (0.468 g, 99% ee) and enantiomer #2 (0.426 g, 98% ee).

Step 2a: (+)-(S)-4-(4-fluorophenyl)-7-({5-[1-hydroxy-1-tifluoromethyl)propyl]-1,3-thiazol-2-yl}thio)-2H-chromen-2-one

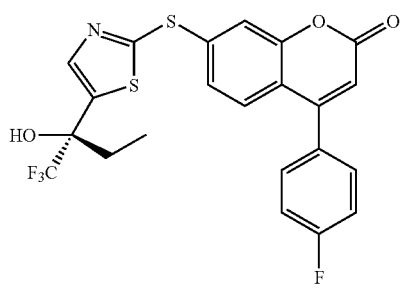

Employing the procedure of Example 1, Step 3, using 7-bromo-4-(4-fluorophenyl)-2H-chromen-2-one (0.307 g, 0.96 mmol), the thiol enantiomer #1 from step 1 of this example (0.234 g, 0.96 mmol) and $K_2CO_3$ (0.400 g, 2.9 mmol) in NMP and heating for 12 h, the title compound was obtained. $[\alpha]^{25}_D$ +16.2° (c=0.26, $CHCl_3$). $^1$H NMR (400 MHz, $CDCl_3$): δ 7.76 (s, 1H), 7.56 (d, 1H), 7.44-7.48 (m, 3H), 7.36 (dd, 1H), 7.25 (m, 2H), 6.39 (s, 1H), 2.93 (br s, 1H), 2.12 (q, 2H), 0.97 (t, 3H).

Step 2b: (−)-(R)-4-(4-fluorophenyl)-7-({5-[1-hydroxy-1-(trifluoromethyl)propyl]-1,3-thiazol-2-yl}thio)-2H-chromen-2-one

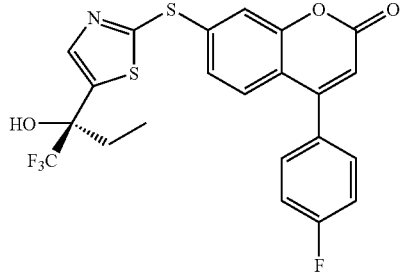

Employing the procedure of Example 1, Step 3, using 7-bromo-4-(4-fluorophenyl)-2H-chromen-2-one (0.307 g, 0.96 mmol), the thiol enantiomer #2 from step 1 of this example (0.234 g, 0.96 mmol) and $K_2CO_3$ (0.400 g, 2.9 mmol) in NMP and heating for 12 h, the title compound was obtained. $[\alpha]^{25}_D$ =−18° (c=0.25, $CHCl_3$). $^1$H NMR (400 MHz, $CDCl_3$): δ 7.76 (s, 1H), 7.56 (d, 1H), 7.44-7.48 (m, 3H), 7.36 (dd, 1H), 7.25 (m, 2H), 6.39 (s, 1H), 2.93 (br s, 1H), 2.12 (q, 2H), 0.97 (t, 3H).

EXAMPLE 8

7-({5-[Dicyclopropyl(hydroxy)methyl]-1,3-thiazol-2-yl}thio)-4-(4-fluorophenyl)2H-chromen-2-one Step 1: Diclopropyl(2-mercapto-1,3-thiazol-5-yl)methanol

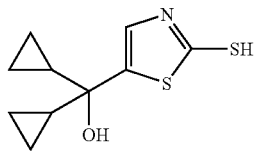

A solution of LDA (59 mmol) in THF was prepared at −10° C. and cooled to −78° C. To the LDA was added a solution of 2-mercaptothiazole (3.00 g, 25.6 mmol) in 5 mL of THF. After 15-20 minute of stirring dicyclopropyl ketone (3.67 g, 33.3 mmol) in 5 mL of THF was added dropwise. After 15 min at −78° C., the temperature was raised to 0° C. and let go for 30 to 60 min. The mixture was quenched with $NH_4Cl$ and diluted with EtOAc. The layers were separated and the aqueous phase was extracted with EtOAc. The combined organic layers were dried over anhydrous $MgSO_4$. The solvent was evaporated and the residue was chromatographed on silica gel (toluene/acetone; 85:15) to give the title compound.

Step 2: 7-({5-[Dicyclopropyl(hydroxyl)methyl]-1,3-thiazol-2-yl}thio)-4-(4-fluorophenyl)-2H-chromen-2-one

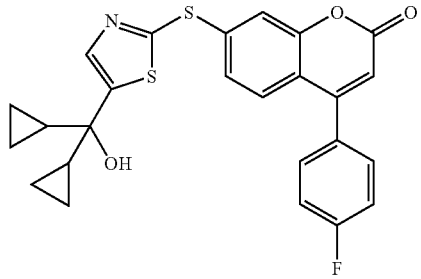

Employing the procedure of Example 1, Step 3, using 7-bromo-4-(4-fluorophenyl)-2H-chromen-2-one (0.300 g, 0.94 mmol), diclopropyl(2-mercapto-1,3-thiazol-5-yl) methanol (0.214 g, 0.94 mmol) and $K_2CO_3$ (0.390 g, 2.8 mmol) and heating in NMP for 10 h gave the title compound. $^1$H NMR (400 MHz, acetone-$d_6$): δ 7.90 (s, 1H), 7.66 (m, 2H), 7.51 (d, 1H), 7.45 (s, 1H), 7.39 (m, 3H), 6.39, (s, 1H), 4.29 (s, 1H), 1.34 (m, 2H), 0.4-0.7 (m, 8H).

EXAMPLE 9

7-({5-[Dicyclopropyl(hydroxy)methyl]-1,3-thiazol-2-yl}thio)-4-pyridin-3-yl-2H-chromen-2-one Step 1: 7-bromo-4-pyridin-3-yl-2H-chromen-2-one

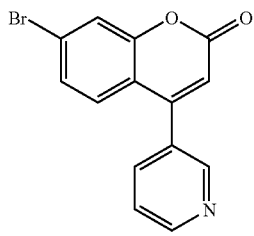

Commercially available 7-hydroxy-4-(3-pyridyl)coumarin (1.48 g, 6.19 mmol) and triphenylphosphine dibromide (5.22 g, 12.4 mmol) were heated in a sand bath at 320-350° for 1.5 h. The cooled solid was taken up with ethanol (200 ml) and silica gel (100 g) and evaporated to dryness. Column chromatography (toluene/acetone; 80:20) gave 0.56 g of the title compound.

Step 2: 7-({5-[dicyclopropyl(hydroxyl)methyl]-1,3-thiazol-2-yl}thio)-4-pyridin-3-yl-2H-chromen-2-one

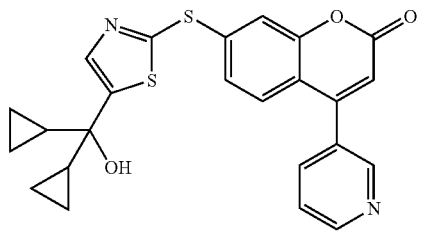

Employing the procedure of Example 1, Step 3, using 7-bromo-4-pyridin-3-yl-2H-chromen-2-one (0.531 g, 1.76 mmol), dicloropyl(2-mercapto-1,3-thiazol-5-yl)methanol (0.400 g, 1.76 mmol) and $K_2CO_3$ (0.730 g, 5.3 mmol) in NMP and heating for 10 h gave the title compound. $^1$H NMR (400 MHz, acetone-$d_6$): δ 8.79 (s, 2H), 8.40 (d, 1H), 7.91 (s, 1H), 7.62 (m, 1H), 7.47 (m, 2H), 7.39 (d, 2H), 4.29 (s, 1H), 1.33 (m, 2H), 0.42-0.68 (m, 8H).

EXAMPLE 10

7-({5-[1,3-Dihydroxy-1-(trifluoromethyl)propyl]-1,3-thiazol-2-yl}thio)-4-(4-fluorophenyl)-2H-chromen-2-one Step 1: 2,2,2-trifluoro-1-(2-mercapto-1,3-thiazol-5-yl)ethanone

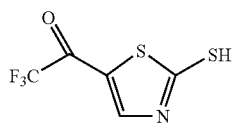

A solution of LDA (95.4 mmol) in THF was prepared at −10° C. and cooled to −78° C. To the LDA was added a solution of 2-mercaptothiazole (10.00 g, 85.3 mmol) in 25 mL of THF. After 15-30 min of stirring, ethyl trifluoroacetate (13.2 mL, 110.9 mmol) in 15 mL of THF was added. The solution was brought to −10° C. and quenched with NH$_4$Cl followed by HCl (10%) and diluted with EtOAc. The layers were separated and the aqueous phase was extracted with EtOAc. The combined organic layers were dried over anhydrous MgSO$_4$. The solvent was evaporated and the residue chromatographed on silica gel (toluene/acetone; 8:2 with 1% methanol) to give the title compound.

Step 2: 3-(1,3-dioxolan-2-yl)-1,1,1-trifluoro-2-(2-mercapto-1,3-thiazol-5-yl-propan-2-ol

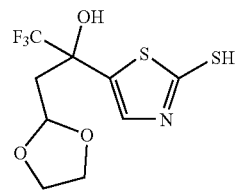

A mixture of magnesium (0.93 g, 38 mmol) and 2-(bromomethyl)-1,3-dioxolane (6.34 g, 38 mmol) was heated to reflux in THF for 3 h. Ketone (1.00 g, 4.69 mmol) of Step 1 in 10 mL of THF was added and the mixture was left under reflux overnight. It was then cooled to rt and quenched with NH$_4$Cl followed by HCl (10%). The layers were separated and the aqueous phase was extracted with EtOAc. The combined organic layers were dried over anhydrous MgSO$_4$. The solvent was evaporated and the residue chromatographed on silica gel (CH$_2$Cl$_2$/CH$_3$OH; 92:8) to give the title compound.

Step 3: 7-({5-[1-(1,3-dioxolan-2-ylmethyl)-2,2,2-trifluoro-1-hydroxyethyl]-1,3-thiazol-2-yl}thio)-4-(4-fluorophenyl)-2H-chromen-2-one

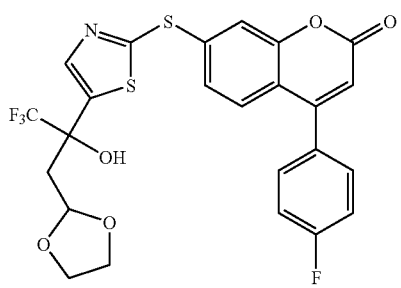

Employing the procedure of Example 1, Step 3, using 7-bromo-4-(4-fluorophenyl)-2H-chromen-2-one (0.319 g, 1.0 mmol), 3-(1,3-dioxolan-2-yl)-1,1,1-trifluoro-2-(2-mercapto-1,3-thiazol-5-yl-propan-2-ol (0.300 g, 1.0 mmol) and K$_2$CO$_3$ (0.414 g, 3.0 mmol) in NMP and heating for 12 h the title compound was obtained. $^1$H NMR (400 MHz, acetone-$d_6$): δ 7.96 (1H), 7.66 (m, 2H), 7.55 (m, 2H), 7.45 (dd, 1H), 7.39 (m, 2H), 6.42 (s, 1H), 6.14 (s, 1H), 5.01 (t, 1H), 3.96 (m, 2H), 3.81 (m, 2H), 2.57 (dd, 1H), 2.43 (dd, 1H).

Step 4: 7-({5-[1,3-dihydroxy-1-trifluoromethyl)propyl]-1,3-thiazol-2-yl}thio)-4-(4-fluorophenyl)-2H-chromen-2-one

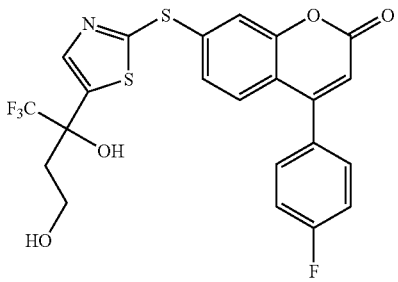

The dioxolane (0.144 g, 0.26 mmol) of Step 3 was heated with p-toluenesulfonic acid (0.025 g, 0.13 mmol) in 1.2 mL of dioxane and 0.6 mL of water for 18 h to furnish the aldehyde. The crude aldehyde was then treated with NaBH$_4$ (0.021 g, 0.56 mmol) to furnish the title compound. $^1$H NMR (400 MHz, acetone-d$_6$): δ 7.90 (s, 1H), 7.68 (m, 2H), 7.62 (s, 1H), 7.56 (dd, 1H), 7.47 (dd, 1H), 7.38 (t, 2H), 6.67 (s, 1H), 6.41 (s, 1H), 4.68 (t, 1H), 3.85 (m, 2H), 2.45 (m, 1H), 2.37 (m, 1H).

EXAMPLE 11

7-({5-[(1R)1,3-dihydroxy-1-(trifluoromethyl)propyl]-1,3-thiazol-2-yl}thio)-4-(4-fluorophenyl)-2H-chromen-2-one Step 1: Methyl(3R)-4,4,4-trifluoro-3-(2-{[4-(4-fluorophenyl)-2-oxo-2H-chromen-7-yl]thio}-1,3-thiazol-5-yl)-3-hydroxybutanoate

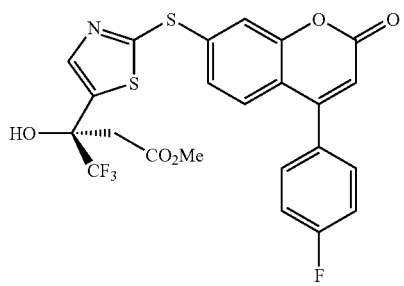

To a solution of (3R)-4,4,4-trifluoro-3-(2-{[4-(4-fluorophenyl)-2-oxo-2H-chromen-7-yl]thio}-1,3-thiazol-5-yl)-3-hydroxybutanoic acid (see example 12, step 4b) (0.140 g, 0.27 mmol) in THF was added an ethereal solution of diazomethane until the evolution of gas was finished. The solvent was removed to yield 0.120 g of the crude title compound. $^1$H NMR (400 MHz, acetone-d$_6$): δ 7.96 (s, 1H), 7.77 (m, 2H), 7.58 (m, 2H), 7.48 (d, 1H), 7.39 (t, 2H), 6.53, (s, 1H), 6.42 (s, 1H), 3.63 (s, 3H), 3.40 (d, 1H), 3.25 (d, 1H).

Step 2: 7-({5-[(1R)-1,3-dihydroxy-1-(trifluoromethyl)propyl]-1,3-thiazol-2-yl}thio)-4-(4-fluorophenyl)-2H-chromen-2-one

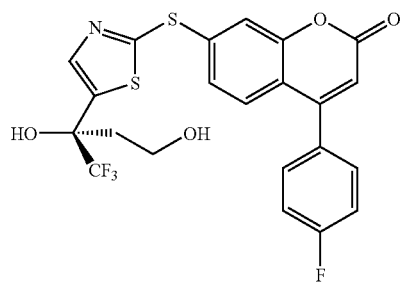

To methyl(3R)-4,4,4-trifluoro-3-(2-{[4-(4-fluorophenyl)-2-oxo-2H-chromen-7-yl]thio}-1,3-thiazol-5-yl)-3-hydroxybutanoate (0.120 g) in THF at −90° C. was added an ethereal solution of LAH 1.0M (0.29 mL) dropwise. After 25 minutes, the solution was quenched with NH$_4$Cl and brought to rt. After extraction with EtOAc, the solution was dried over MgSO$_4$ and the solvent removed under vacuum. This crude mixture was then treated with NaBH$_4$ in methanol at 0° C. for 15 minute. The mixture was quenched with NH$_4$Cl and extracted with EtOAc. After flash chromatography on silica gel (hexane/EtOAc; 55:45) the title compound was isolated. $^1$H NMR (400 MHz, acetone-d$_6$): δ 7.90 (s, 1H), 7.68 (m, 2H), 7.62 (s, 1H), 7.56 (dd, 1H), 7.47 (dd, 1H), 7.38 (t, 2H), 6.67 (s, 1H), 6.41 (s, 1H), 4.68 (t, 1H), 3.85 (m, 2H), 2.45 (m, 1H), 2.37 (m, 1H).

EXAMPLE 12

(+)-(3R) and (−)-(3S)-4,4,4-Trifluoro-3-(2-{[4-(4-fluorophenyl)-2-oxo-2H-chromen-7-yl]thio}-1,3-thiazol-5-yl)-3-hydroxybutanoic acid Step 1: (±)-Methyl-4,4,4-trifluoro-3-hydroxy-3-(2-mercapto-1,3-thiazol-5-yl)butanoate

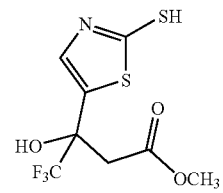

A solution of LDA (164 mmol) in THF was prepared at −10° C. and cooled to −78° C. After 15 min, methyl acetate (13.1 ml, 164 mmol) in THF (20 ml) was added to the reaction. After 5 min, 2,2,2-trifluoro-1-(2-mercapto-1,3-thiazol-5-yl)ethanone (15.2 g, 71.2 mmol), in THF (70 ml) was added. The reaction mixture was brought to −10° C. and partitioned between aqueous NH$_4$Cl and EtOAc. The layers were separated and the aqueous phase was extracted with EtOAc. The combined organic layers were washed with HCl 10%, brine and dried over anhydrous MgSO$_4$. The solvent was evaporated and the product triturated with hexane/ether to give the racemic titled compound.

Step 2: Separation on chiral HPLC column of methyl-4,4,4-trifluoro-3-hydroxy-3-(2-mercapto-1,3-thiazol-5-yl)butanoate

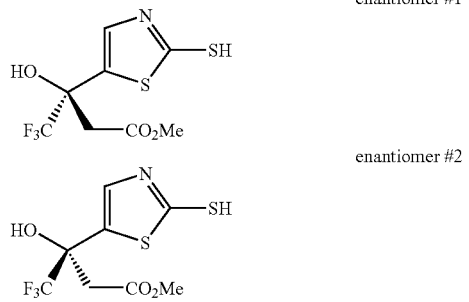

enantiomer #1 enantiomer #2

A solution of methyl-4,4,4-trifluoro-3-hydroxy-3-2-mercapto-1,3-thiazol-5-yl)butanoate (2.0 g) in EtOH/hexane (30 ml, 1:1) was injected (1×2.0 g) onto a CHIRALPAK AD preparative (5 cm×50 cm) HPLC column (eluting with hexane/EtOH; 7:3 at 75 ml/min with UV detection at 300 nm). The enantiomers were separated with the faster eluting enantiomer having a retention time of ~18 min (enantiomer #1) and the slower eluting enantiomer having a retention time of ~36 min (enantiomer #2). The enantiomers were concentrated to provide enantiomer #1 (99% ee) and enantiomer #2 (99% ee).

Step 3a: (3S)-4,4,4-Trifluoro-3-hydroxy-3-(2-mercapto-1,3-thiazol-5-yl)butanoic acid

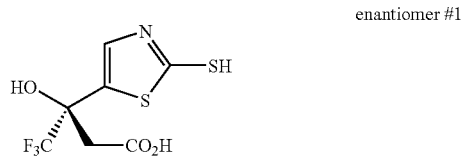

enantiomer #1

To a solution of (3S)-methyl-4,4,4-trifluoro-3-hydroxy-3-(2-mercapto-1,3-thiazol-5-yl)butanoate (enantiomer #1, 7.54 g, 26.2 mmol) in THF (80 ml) and MeOH (40 ml) was added a solution of KOH (39 ml, 2.67 N, 105 mmol). The mixture was heated at 45° C. for 4 h then cooled to room temperature. The reaction mixture was diluted in EtOAc, washed with HCl 10%, brine and dried over MgSO$_4$. The solvent was evaporated to give the title compound in quantitative yield.

Step 3b: (3R)-4,4,4-trifluoro-3-hydroxy-3-(2-mercapto-1,3-thiazol-5-yl)butanoic acid

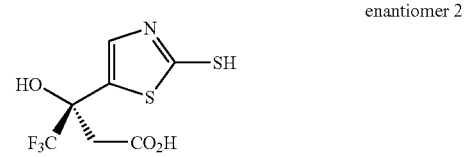

enantiomer 2

Following the procedure of Step 3a, with (3R)-methyl-4,4,4-trifluoro-3-hydroxy-3-(2-mercapto-1,3-thiazol-5-yl)butanoate (enantiomer #2, 6.74 g, 23.4 mmol), KOH (35 ml, 2.67 N, 93.8 mmol) in THF and MeOH the title compound was obtained in quantitative yield.

Step 4a: (3S)-4,4,4-trifluoro-3-(2-{[4-(4-fluorophenyl)-2-oxo-2H-chromen-7-yl]thio}-1,3-thiazol-5-yl)-3-hydroxybutanoic acid

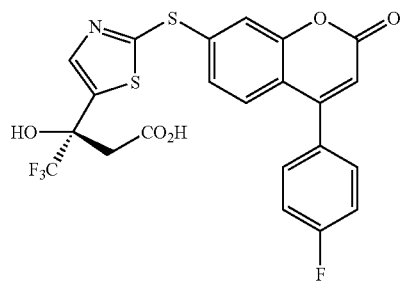

Employing the procedure of Example 1, Step 3, using 7-bromo-4-(4-fluorophenyl)-2H-chromen-2-one (0.467 g, 1.5 mmol), (3S)-4,4,4-trifluoro-3-hydroxy-3-(2-mercapto-1,3-thiazol-5-yl)butanoic acid (enantiomer #1, 0.400 g, 1.5 mmol) and potassium carbonate (0.708 g, 5.1 mmol) in NMP at 120° C., the title compound was obtained. Purification was done on silica gel (CH$_2$Cl$_2$/MeOH/HOAc; 90:10:0.5). $[\alpha]^{25}_D$–30° (c=0.5, CHCl$_3$). $^1$H NMR (400 MHz, acetone-d$_6$): δ 7.99 (s, 1H), 7.68 (m, 2H), 7.58 (m, 2H), 7.48 (dd, 1H), 7.39 (dd, 2H), 6.43 (s, 1H), 3.33 (dd, 2H).

Step 4b: (3R)-4,4,4-trifluoro-(3-2-{[4-(4-fluorophenyl)-2-oxo-2H-chromen-7-yl]thio}-1,3-thiazol-5-yl)-3-hydroxybutanoic acid

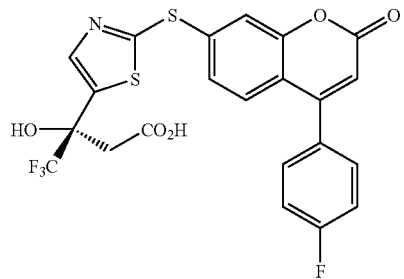

Employing the procedure of Example 1, Step 3, using 7-bromo-4-(4-fluorophenyl)-2H-chromen-2-one (0.488 g, 1.5 mmol), the (3R)-4,4,4-trifluoro-3-hydroxy-3-(2-mercapto-1,3-thiazol-5-yl)butanoicacid (enantiomer #2, 0.420 g, 1.5 mmol) and potassium carbonate (0.740 g, 5.3 mmol) in NMP at 120° the title compound was obtained. Purification was done on silica gel (CH$_2$Cl$_2$/MeOH/HOAc; 90:10:0.5) to give the title compound. $[\alpha]^{25}_D$+32° (c=1, CHCl$_3$). $^1$H NMR (400 MHz, acetone-d$_6$): δ 7.99 (s, 1H), 7.68 (m, 2H), 7.58 (m, 2H), 7.48 (dd, 1H), 7.39 (dd, 2H), 6.43 (s, 1H), 3.33 (dd, 2H).

EXAMPLE 13

7-{[5-(1-Methylpropyl)-1,3-thiazol-2-yl]thio}-4-(4-fluorophenyl)-2H-chromen-2-one Step 1: 2-(2-Mercapto-1,3-thiazole-5-yl)butan-2-ol

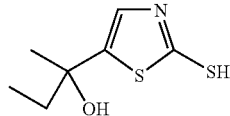

A solution of LDA (59 mmol) in THF was prepared at −10° C. and cooled to −78° C. To the LDA was added a solution of 2-mercaptothiazole (3.00 g, 25.6 mmol) in 5 mL of THF. After 15-20 min of stirring a solution of 2-butanone (2.23 mL, 38.4 mmol) was added, and the reaction mixture was stirred at −78° C. for 2 h. The reaction mixture was diluted with ether and washed successively with aq. 2N HCl, $H_2O$ and brine, dried over $MgSO_4$, filtered and concentrated. The crude product was washed with $Et_2O$ to give the title compound.

Step 2: 4-(4-fluorophenyl)-7-{[5-(1-hydroxy-1-methylpropyl)-1,3-thiazol-2-yl]thio}-2H-chromen-2-one

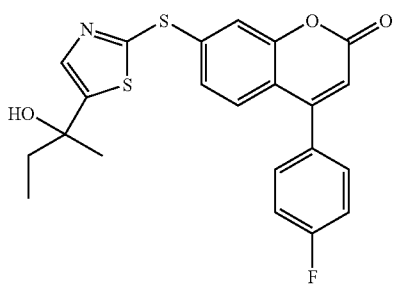

Employing the procedure described in Example 1, Step 3, using 7-bromo-4-(4-fluorophenyl)-2H-chromen-2-one, 2-(2-mercapto-1,3-thiazole-5-yl)butan-2-ol and $K_2CO_3$ in NMP, the title compound was obtained. $^1$H NMR (400 MHz, acetone-$d_6$): δ 7.72 (s, 1H), 7.63-7.68 (m, 2H), 7.51 (d, 1H), 7.43 (d, 1H), 7.33-7.41 (m, 3H), 6.38 (s, 1H), 1.93-1.80 (m, 2H), 1.61 (s, 3H), 0.90 (t, 3H).

EXAMPLE 14

7-[(5-sec-Butyl-1,3-thiazol-2-yl)thio]-4-(4-fluorophenyl)-2H-chromen-2-one

Step 1: 5-sec-Butyl-1,3-thiazole-2-thiol

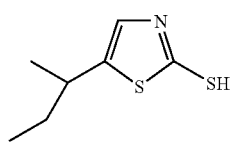

Following the procedure described in Example 4, Step 2, but substituting the alcohol therein with 2-(2-mercapto-1,3-thiazole-5-yl)butan-2-ol, the title compound was obtained.

Step 2: 7-[(5-sec-butyl-1,3-thiazol-2-yl)thio]-4-(4-fluorophenyl)-2H-chromen-2-one

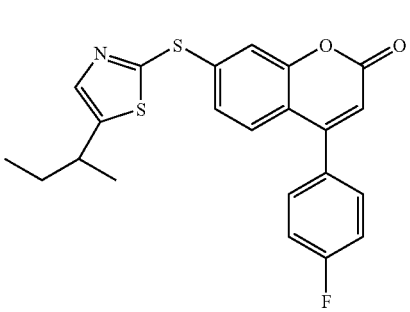

Employing the procedure described in Example 1, Step 3, but using 7-bromo-4-(4-fluorophenyl)-2H-chromen-2-one, 5-sec-butyl-1,3-thiazole-2-thiol and $K_2CO_3$, the title compound was obtained. $^1$H NMR (400 MHz, acetone-$d_6$): δ 7.58-7.67 (m, 3H), 7.52 (d, 1H), 7.46 (d, 1H), 7.32-7.42 (m, 3H), 6.38 (s, 1H), 3.08 (sextet, 1H), 1.83-1.67 (m, 2H), 1.32 (d, 3H), 0.89 (t, 3H).

EXAMPLE 15

7-{[4-(1-Ethyl-hydroxypropyl)-1,3-thiazol-2-yl]thio}-4-(4-fluorophenyl)-2H-chromen-2-one Step 1: 3-(2-Mercapto-1,3-thiazol-4-yl)pentan-3-ol

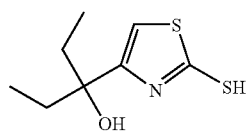

To a solution of ethyl 2-mercapto-1,3-thiazole-4-carboxylate ((Ref: *J. Am. Chem. Soc.* 1935, 57, 1127), 0.694 g, 3.67 mmol) in $Et_2O$ (40 mL) at 0° C. was added EtMgBr (3 M in $Et_2O$, 2.7 mL, 8.07 mmol). The reaction mixture was heated to reflux for 15 min, quenched with $NH_4Cl$, extracted with 3 portions of $Et_2O$, dried over $MgSO_4$, filtered and concentrated in vacuo. The crude material was treated with more EtMgBr (3 M in $Et_2O$, 6 mL, 18 mmol) at rt for 10 min, quenched, extracted and isolated in the same way. The residue was washed with $Et_2O$ and $Et_2O$/hexane to afford the title compound.

Step 2: 7-{[4-(1-ethyl-1-hydroxypropyl)-1,3-thiazol-2-yl]thio}-4-(4-fluorophenyl)-2H-chromen-2-one

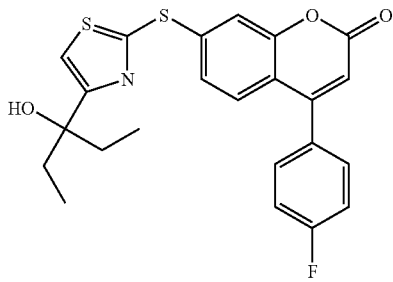

Employing the procedure described in Example 1, Step 3, using 7-bromo-4-(4-fluorophenyl)-2H-chromen-2-one and the previous thiol 3-2-mercapto-1,3-thiazol-4-yl)pentan-3-ol, the title compound was obtained. $^1$H NMR (400 MHz, acetone-$d_6$) δ 7.67-7.61 (m, 2H), 7.56 (s, 1H), 7.51 (d, 1H), 7.46-7.30 (m, 4H), 6.37 (s, 1H), 2.04-1.88 (m, 2H), 1.88-1.70 (m, 2H), 0.78 (t, 6H).

EXAMPLE 16

(+) and (−) 7-{[5-Cyclopropyl-2,2,2-trifluoro-1-hydroxymethyl)-1,3-thiazol-2-yl]thio}-4-(4-fluorophenyl)-2H-chromen-2-one Step 1: (±)-1-Cyclopropyl-2,2,2-trifluoro-1-(2-mercapto-1,3-thiazol-5-yl)ethanol

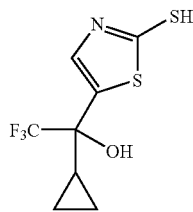

Cyclopropylmagnesium bromide (0.5 M in THF, 7.00 mL, 3.52 mmol) was added dropwise to solution of 2,2,2-trifluoro-1-(2-mercapto-1,3-thiazol-5-yl)ethanone (0.300 g, 1.41 mmol) in THF(3 mL) at 0° C. After 1 h, saturated aqueous NH$_4$Cl was added and the aqueous layer was extracted with EtOAc (3×). The combined organics were washed with brine, dried (Na$_2$SO$_4$) and concentrated. The residue was purified by chromatography on silica gel (toluene/acetone; 85:15) to yield the title compound.

Step 2: Separation on chiral HPLC of (−)- and (+)-1-cyclopropyl-2,2,2-trifluoro-1-(2-mercapto-1,3-thiazol-5-yl)ethanol A solution of (±)-1-cyclopropyl-2,2,2-trifluoro-1-(2-mercapto-1,3-thiazol-5-yl)ethanol (8.00 g) in 25:75 EtOH/hexane (10 mL) was injected (1×0.600 g) onto a CHIRALPAK AD preparative (5 cm×50 cm) HPLC column (eluting with EtOH/hexane; 15:85, at 75 ml/min with UV detection at 300 nm). The enantiomers were separated with the faster eluting enantiomer having a retention time of ~28 min. [(−)-enantiomer #1] and the slower eluting enantiomer having a retention time of ~38 min. [(+)-enantiomer #2]. The eluants were concentrated to provide (−)-enantiomer #1 {>99% ee, [α]$_D$=−79.3° (c=1, EtOH)} and (+)-enantiomer #2 {>99% ee, [α]$_D$=+79.4° (c=1, EtOH)}.

Step 3a: (+)-7-{[5-(1-cyclopropyl-2,2,2-trifluoro-1-hydroxyethyl)-1,3-thiazol-2-yl]thio}-4-(4-fluorophenyl)-2H-chromen-2-one Employing the procedure described in Example 1, Step 3, with 7-bromo-4-(4-fluorophenyl)-2H-chromen-2-one, (+)-1-cyclopropyl-2,2,2-trifluoro-1-(2-mercapto-1,3-thiazol-5-yl)ethanol and potassium carbonate in NMP at 120° C., the title compound was obtained. $^1$H NMR (400 MHz, acetone-$d_6$): δ 8.00 (s, 1H), 7.68 (m, 2H), 7.56-7.60 (m, 2H), 7.48 (dd, 1H), 7.39 (t, 2H), 6.43 (s, 1H), 5.88 (s, 1H), 1.65 (m, 1H), 0.82 (m, 1H), 0.54-0.71 (m, 3H); [α]$_D$=+29.4° (c=1, EtOH).

Step 3b: (−)-7-{[5-(1-cyclopropyl-2,2,2-trifluoro-1-hydroxyethyl)-1,3-thiazol-2-yl]thio}-4-(4-fluorophenyl)-2H-chromen-2-one Employing the procedure described in Example 1, Step 3, using 7-bromo-4-(4-fluorophenyl)-2H-chromen-2-one and (−)-1-cyclopropyl-2,2,2-trifluoro-1-(2-mercapto-1,3-thiazol-5-yl)ethanol, the titled compound was obtained. $^1$H NMR (400 MHz, acetone-$d_6$): δ 8.00 (s, 1H), 7.68 (m, 2H), 7.56-7.60 (m, 2H), 7.48 (dd, 1H), 7.39 (t, 2H), 6.43 (s, 1H), 5.88 (s, 1H), 1.65 (m, 1H), 0.82 (m, 1H), 0.54-0.71 (m, 3H); [α]$_D$=−29.6° (c=1, EtOH).

EXAMPLE 17

(−) and (+)-7-{[5-(1-Cyclopropyl-2,2,2-trifluoro-1-hydroxyethyl)-1,3-thiazol-2-yl]thio}-4-pyridin-3-ul-2H-chromen-2-one Step 1a: (−)-7-{[5-(1-Cyclopropyl-2,2,2-trifluoro-1-hydroxyethyl)-1,3-thiazol-2-yl]thio}-4-pyridin-3-yl-2H-chromen-2-one

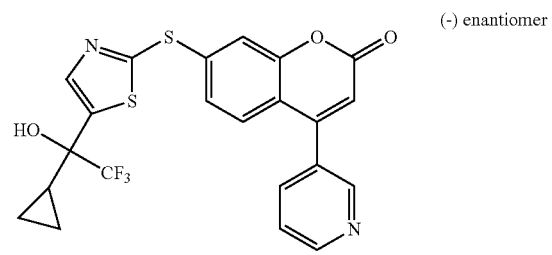
(−) enantiomer

Powdered KOH (0.111 g, 1.98 mmol) was added to a solution of (−)-1-cyclopropyl-2,2,2-trifluoro-1-(2-mercapto-1,3-thiazol-5-yl)ethanol (0.507 g, 1.98 mmol) in dry MeOH (2 mL). When a solution was obtained, the reaction mixture was concentrated to dryness. Dry toluene was then added and the mixture was concentrated to dryness again. The residue was dissolved in NMP (2 mL) and 7-bromo-4-pyridin-3-yl-2H-chromen-2-one (0.500 g, 1.65 mmol) was added and the resulting mixture was stirred at 120° C. for 16 h. Once cooled, the mixture was directly applied onto a column of silica gel and chromatographed (acetone/toluene 5:95 to 20:80), affording the title compound. $^1$H NMR (500 MHz, CDCl$_3$): δ 8.76 (brd, 1H), 8.68 (d, 1H), 7.85 (s, 1H), 7.79 (brd, 1H), 7.50

(m, 2H), 7.31-7.36 (m, 2H), 6.39 (s, 1H), 3.05 (br s, 1H), 1.48 (m, 1H), 0.71 (m, 2H), 0.62 (m, 1H), 0.56 (m, 1H); [α]$_D$=−31.1° (c=1.05, EtOH).

Step 1b: (+)-7-{[5-(1-cyclopropyl-2,2,2-trifluoro-1-hydroxyethyl)-1,3-thiazol-2-yl]thio}-4-pyridin-3-yl-2H-chromen-2-one

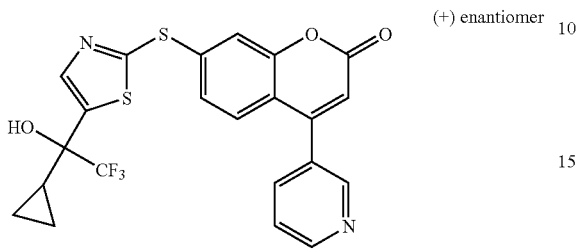

(+) enantiomer

Employing the procedure described in Step 1a of this Example using (+)-1-cyclopropyl-2,2,2-trifluoro-1-(2-mercapto-1,3-thiazol-5-yl)ethanol, the title compound was obtained. $^1$H NMR (400 MHz, acetone-d$_6$): δ 8.78-8.80 (m, 2H), 8.04 (dt, 1H), 8.00 (s, 1H), 7.61-7.64 (m, 2H), 7.54 (d, 1H), 7.49 (dd, 1H), 6.52 (s, 1H), 5.90 (s, 1H), 1.65 (m, 1H), 0.82 (m, 1H), 0.54-0.71 (m, 3H); [α]$_D$=+30.1° (c=1, EtOH).

EXAMPLE 18

7-({5-[(1S and 1R)-1-Hydroxy-1-(trifluoromethyl)propyl]-1,3-thiazol-2-yl}thio)-4-phenyl-2H-chromen-2-one Step 1: 7-hydroxy-4-phenyl-2H-chromen-2-one

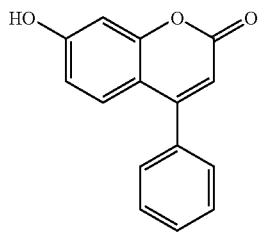

Concentrated H$_2$SO$_4$ (65 ml) was added to a mixture of resorcinol (26.7 g, 242.4 mmol) and ethyl benzoylacetate (51.26 g, 266.7 mmol) at 0° C. The resulting suspension was stirred for 24 h at room temperature. Water (2 L) was added and the mixture was stirred for 1 h. The solid was filtered, washed with water (2 L) and dried to give 55.78 g of the titled compound.

Step 2: 7-Bromo-4-phenyl-2H-chromen-2-one

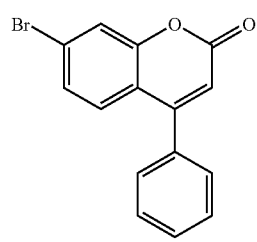

7-hydroxy-4-phenyl-2H-chromen-2-one, (5.07 g, 21.3 mmol) and triphenylphosphine dibromide (9.88 g, 23.4 mmol) were heated in a sand bath at 320-350° C. for 3 h. The cooled mixture was dissolved in dichloromethane, silica gel (150 g) was added and the mixture was evaporated. Column chromatography with hexane/EtOAc: 70:30, gave the title compound.

Step 3: 7-({5-[(1S)-1-hydroxy-1-(trifluoromethyl)propyl]-1,3-thiazol-2-yl}thio)-4-phenyl-2H-chromen-2-one

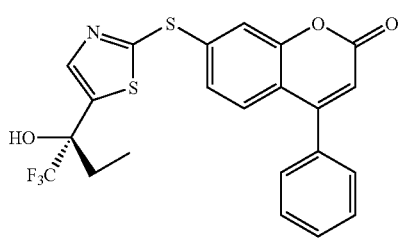

Employing the procedure of Example 1, Step 3, using 7-bromo-phenyl-2H-chromen-2-one (0.331 g, 1.1 mmol), thiol enantiomer #1 (0.243 g, 1 mmol) of Example 7, Step 1, and potassium carbonate (0415 g, 3 mmol) in NMP and heating at 120° C. for 20 h, the title compound was obtained. $^1$H NMR (400 MHz, acetone-d$_6$): δ 7.88 (s, 1H), 7.45-7.62 (m, 8H), 6.41 (s, 1H), 6.10 (s, 1H, OH), 2.19 (q, 2H), 0.94 (t, 3H).

Step 4: 7-({5-[(1R)-1-Hydroxy-1-(trifluoromethyl)propyl]-1,3-thiazol-2-yl}thio)-4-phenyl-2H-chromen-2-one

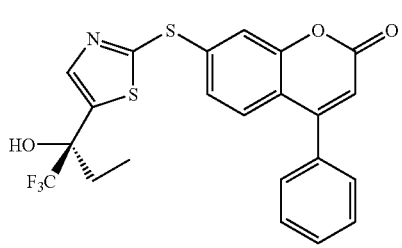

Following the procedure of Step 3 in this Example, using thiol enantiomer #2 of Example 7, Step 1, the title compound was obtained. $^1$H NMR (400 MHz, acetone-d$_6$): δ 7.88 (s, 1H), 7.45-7.62 (m, 8H), 6.41 (s, 1H), 6.10 (s, 1H, OH), 2.19 (q, 2H), 0.94 (t, 3H).

EXAMPLE 19

4-(4-Fluorophenyl)-8-methyl-7-({5-[2,2,2-trifluoro-1-hydroxy-1-(trifluoromethyl)ethyl]-1,3-thiazol-2-yl}thio)-2H-chromen-2-one Step 1: 4-(4-fluorophenyl)-7-hydroxy-8-methyl-2-H-chromen-2-one

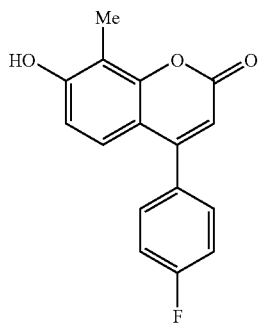

Concentrated $H_2SO_4$ (27 ml) was added to a mixture of methyl resorcinol (12.41 g, 100 mmol) and methyl-4-fluorobenzoylacetate (21.8 g, 110 mmol) at 0° C. The resulting suspension was set aside for 40 h. Water (1 L) was added and the mixture was stirred for 1 h. The residue was filtered, washed with water (2 L) and dried to give the title compound.

Step 2: 7-bromo-4-(4-fluorophenyl)-8-methyl-2H-chromen-2-one

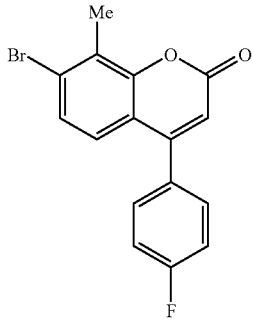

4-(4-fluorophenyl)-7-hydroxy-8-methyl-2-H-chromen-2-one, (4.47 g, 16.5 mol) and triphenylphosphine dibromide (7.68 g, 18.2 mmol) were heated in a sand bath at 320-350° C. for 0.5 h. The cooled mixture was dissolved in dichloromethane, silica gel was added and the mixture was evaporated. Chromatography on silica gel (hexane/EtOAC; 90:10), gave the title compound.

Step 3: 4-(4-fluorophenyl)-8-methyl-7-({5-[2,2,2-trifluoro-1-hydroxy-1-trifluoromethyl)ethyl)]-1,3-thiazol-2-yl}thio)-2-chromen-2-one

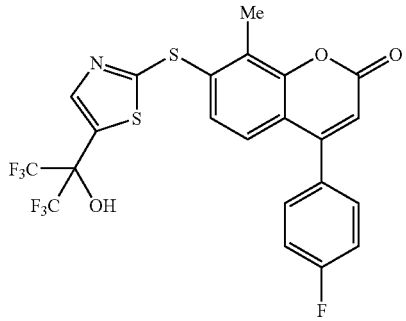

Employing the procedure of Example 1, Step 3 using 1,1,1,3,3,3-hexafluoro-2-(2-mercapto-1,3-thiazol-5-yl)propan-2-ol, (0.332 g, 1.2 mmol), 7-bromo-4-(4-fluorophenyl)-8-methyl-2H-chromen-2-one (0.430 g, 1.3 mmol) and potassium carbonate (0.404 g, 2.9 mmol) in NMP, the title compound was obtained. $^1$H NMR (400 MHz, acetone-$d_6$): δ 8.21 (s, 1H, OH), 7.97 (s, 1H), 7.36-7.72 (m, 6H), 6.50 (s, 1H), 2.67 (s, 3H).

EXAMPLE 20

4-(3,5-Difluorophenyl)-7-({5-[1-hydroxy-1(trifluoromethyl)propyl]-1,3-thiazol-2-yl}thio)-2H-chromem-2-one Step 1: 3-fluorophenylacetate

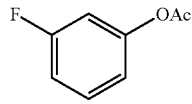

To a solution of 3-fluorophenol (100 g, 0.89 mol) in dry $CH_2Cl_2$ was added pyridine (79.4 mL, 0.98 mol) followed dropwise by acetyl chloride (88.4 mL, 0.94 mol). The reaction mixture was stirred for 2 h at 50° C. and then diluted with EtOAc and $Et_2O$ The organic phase was washed successively with HCl 1N (2×), $H_2O$, brine, dried over $Na_2SO_4$ and evaporated to give the title compound.

Step 2: 1-(4-fluoro-2-hydroxyphenyl)ethanone

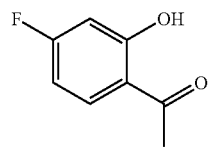

To 122 g (0.79 mol) of 3-fluorophenylacetate was added $AlCl_3$(137 g, 1.03 mol) and the resulting mixture was heated at 160° C. for 1.5 h then cooled at 0° C. HCl 1N was carefully added followed by $Et_2O$. The aqueous phase was extracted (2×) with Et$_2$O and the combined organic phase washed with brine, dried over Na$_2$SO$_4$ and evaporated to give the title compound.

Step 3: 7-fluoro-4-hydroxy-2H-chromen-2-one

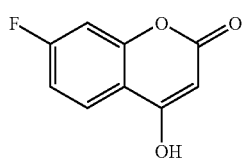

A solution of 1-(4-fluoro-2-hydroxyphenyl)ethanone (50 g, 0.33 mol) in toluene was added over 30 min to a suspension of NaH (60% oil, 65 g, 1.63 mol) in toluene. Then diethylcarbonate (59 mL, 0.49 mol) was added over 15 min and the reaction mixture was stirred at 115° C. for 6 h. The mixture was cooled to rt followed by the addition of HCl 2N and diluted with EtOAc. The organic phase was washed with brine, dried over Na$_2$SO$_4$ and evaporated. The residue was purified by trituration in hexane and Et$_2$O to give the title compound.

Step 4: 7-fluoro-2-oxo-2H-chromen-4-yl-trifluoromethanesulfonate

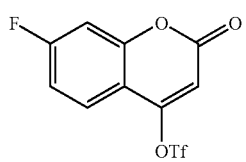

To a solution of 7-fluoro-4-hydroxy-2H-chromen-2-one (10 g, 55.5 mmol) in CH$_2$Cl$_2$ at −10° C. was added Et$_3$N (10 mL, 71.7 mmol) followed by trifluoromethanesulfonic anhydride (11.2 mL, 66.6 mmol) and stirred for 2 h. A solution of NH$_4$Cl was added and the reaction mixture was diluted with EtOAc. The organic phase was washed with H$_2$O, brine, dried over Na$_2$SO$_4$ and evaporated. The residue was purified by flash chromatography on silica gel using toluene/CH$_2$Cl$_2$, 1:1 to 100% CH$_2$Cl$_2$ to give the title compound.

Step 5: 4-(3,5-difluorophenyl)-fluoro-2H-chromen-2-one

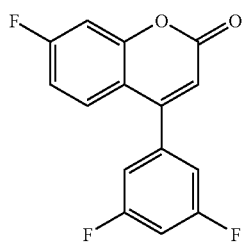

To a solution of 7-fluoro-2-oxo-2H-chromen-4-yl-trifluoromethanesulfonate (1.0 g, 3.2 mmol) in dioxane was added 3,5-difluorophenyl boronic acid (0.658 g, 4.2 mmol), PdCl$_2$(PPh$_3$)$_2$ (0.112 g, 0.16 mmol) and KF (0.744 g, 12.8 mmol). The mixture was heated at 90° C. overnight, cooled and partitioned between aqueous NH$_4$Cl and EtOAc. The layers were separated and the aqueous phase was extracted with EtOAc. The combined organic layers were washed with brine and dried over anhydrous Na$_2$SO$_4$. The solvent was evaporated and the residue chromatographed on silica gel (toluene/acetone; 95:5) to give the title compound.

Step 6: 4-(3,5-difluorophenyl)-7-({5-[1-hydroxy-1-(trifluoromethyl)propyl]-1,3-thiazol-2-yl}thio)-2H-chromen-2-one

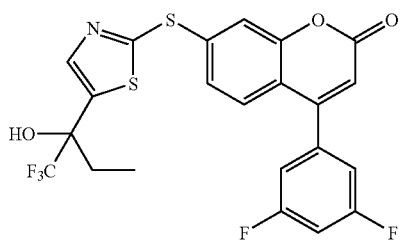

A solution of 4-(3,5-difluorophenyl)-fluoro-2H-chromen-2-one (0.258 g, 0.93 mmol), 1,1,1-trifluoro-2-(2-mercapto-1,3-thiazol-5-yl)butan-2-ol, (0.250 g, 1.03 mmol) and potassium carbonate (0.387 g, 2.8 mmol) in NMP was heated at 120° C. overnight. The mixture was cooled to room temperature and partitioned between aqueous NH$_4$Cl and EtOAc. The layers were separated and the aqueous phase was extracted with EtOAc. The combined organic layers were washed with water, brine and dried over anhydrous Na$_2$SO$_4$. The solvent was evaporated and the residue chromatographed on silica gel (toluene/acetone; 95:5) to give the title compound. $^1$H NMR (400 MHz, CDCl$_3$): δ 7.78 (s, 1H), 7.56 (d, 1H), 7.43 (d, 1H), 7.37 (dd, 1H), 7.00-7.04 (m, 3H), 6.41 (s, 1H), 2.66 (br s, 1H), 2.12 (q, 2H), 0.98 (t, 3H).

EXAMPLE 21

4-[3-(Cyclopropyloxy)phenyl]-7-({5-[1-hydroxy-1-(trifluoromethyl)propyl]-1,3-thiazol-2-yl}thio)-2H-chromen-2-one Step 1: 4-[3-(cyclopropyloxy)phenyl]-7-fluoro-2H-chromen-2-one

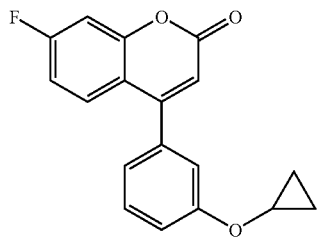

Employing the procedure of Example 20, Step 5, with [3-(cyclopropyloxy)phenyl]-boronic acid the title compound was obtained.

Step 2: 4-[3-(cyclopropyloxy)phenyl]-7-({5-[1-hydroxy-1-(trifluoromethyl)propyl]-1,3-thiazol-2-yl}thio)-2H-chromen-2-one

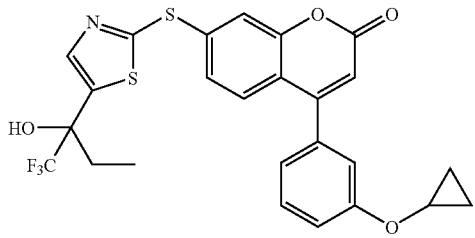

Employing the procedure of Example 1, Step 3, but using 4-[3-cyclopropyloxy)phenyl]-7-fluoro-2H-chromen-2-one, the title compound was obtained. ¹H NMR (400 MHz, CDCl₃): δ 7.76 (s, 1H), 7.52-7.59 (m, 2H), 7.47 (t, 1H), 7.36 (dd, 1H), 7.22 (dd, 1H), 7.11 (m, 1H), 7.05 (d, 1H), 6.41 (s, 1H), 3.79 (m, 1H), 2.61 (br s, 1H), 2.12 (q, 2H), 0.98 (t, 3H).

EXAMPLE 22

4-(3-Methoxyphenyl)-7-({5-[2,2,2-trifluoro-1-hydroxy-1-(trifluoromethyl)propyl]-1,3-thiazol-2-yl}thio-2H-chromen-2-one

Step 1:
7-bromo-4-(3-methoxyphenyl)-2H-chromen-2-one

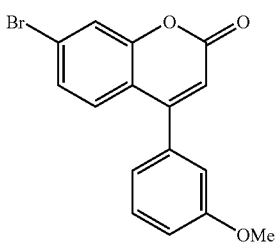

Following the procedure of Example 1, Step 1, with 3-methoxyphenylboronic acid the title compound was obtained.

Step 2: 4-(3-methoxyphenyl)-7-({5-[(2,2,2-trifluoro-1-hydroxy-1-(trifluoromethyl)propyl]-1,3-thiazol-2-yl}thio-2H-chromen-2-one

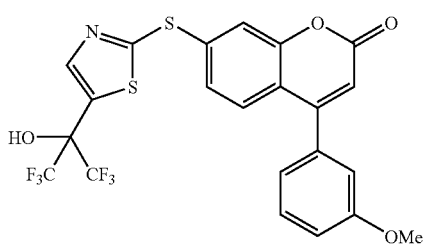

Employing the procedure of Example 1, Step 3, but using 7-bromo-4-(3-methoxyphenyl)-2H-chromen-2-one, the title compound was obtained. ¹H NMR (400 MHz, CDCl₃): δ 7.95 (s, 1H), 7.63 (d, 1H), 7.59 (d, 1H), 7.47 (t, 1H), 7.42 (dd, 1H), 7.09 (dd, 1H), 7.03 (d, 1H), 6.98 (s, 1H), 6.45 (s, 1H), 4.35 (s, 1H), 3.89 (s, 3H).

EXAMPLE 23

7-({5-[(1R)-Hydroxy-1-(trifluoromethyl)propyl]-1,3-thiazol-2-yl}thio)-4-(3-methoxyphenyl)-2H-chromen-2-one

Step 1: 7-({5-[(1R)-hydroxy-1-trifluoromethyl)propyl]-1,3-thiazol-2-yl}thio)-4-(3-methoxyphenyl)-2H-chromen-2-one

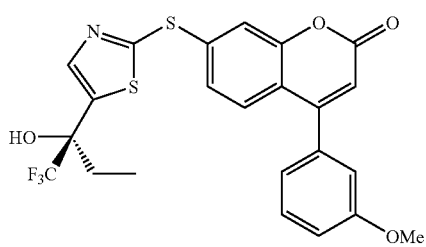

Employing the procedure of Example 1, Step 3, but using 7-bromo-4-(3-methoxyphenyl)-2H-chromen-2-one, and thiol enantiomer #2 of Example 7, Step 1 as the starting materials, the title compound was obtained. ¹H NMR (400 MHz, CDCl₃): δ 7.76 (s, 1H), 7.51-7.59 (m, 2H), 7.48 (t, 1H), 7.36 (dd, 1H), 7.09 (dd, 1H), 7.03 (d, 1H), 6.98 (m, 1H), 6.41 (s, 1H), 3.89 (s, 3H), 2.60 (br s, 1H), 2.12 (q, 2H), 0.98 (t, 3H).

EXAMPLE 24A 7-({5-[(1R)-Hydroxy-1-(trifluoromethyl)propyl]-1,3-thiazol-2-yl}thio)-4-pyridin-3-yl-2H-chromen-2-one

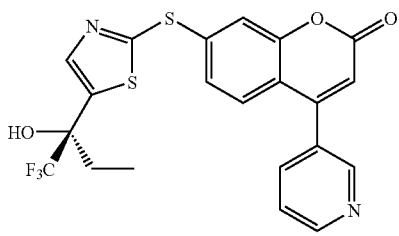

KOH (0.223 g, 3.97 mmol) was added to a solution of (2R)-1,1,1-trifluoro-2-(2-mercapto-1,3-thiazol-5-yl)butan-2-ol (0.966 g, 3.97 mmol) in dry MeOH. When a solution was obtained, the reaction mixture was concentrated to dryness. Dry toluene was then added and the mixture was concentrated to dryness again. The residue was dissolved with 7-bromo-4-pyridin-3-yl-2H-chromen-2-one (1.0 g, 3.31 mmol) in NMP, and the resulting mixture was stirred at 120° C. for 16 h. Once cooled, the mixture was directly applied onto a column of silica gel and chromatographed (acetone/toluene; 5:95 to 15:85), affording the title compound. ¹H NMR (400 MHz, CDCl₃): δ 8.81 (dd,1H), 8.72 (dd, 1H), 7.82 (dt, 1H), 7.78 (s, 1H), 7.51-7.59 (m, 2H), 7.33-7.40 (m, 2H), 6.42 (s, 1H), 2.88 (br s, 1H), 2.12 (q, 2H), 0.99 (t, 3H).

EXAMPLE 24B 7-({5-[(1S)-Hydroxy-1-(trifluoromethyl)propyl]-1,3-thiazol-2-yl}thio)-4-pyridin-3-yl-2H-chromen-2-one Step 1: 7-fluoro-4-pyridin-3-yl-2H-chromen-2-one

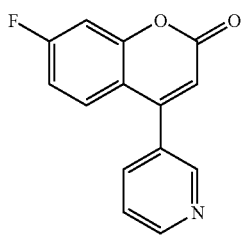

To a solution of 3-bromopyridine (0.679 mL, 7.05 mmol) in THF at −100° C. was added butyl lithium (2.82 mL, 2.5 M/hexane, 7.05 mmol). After 10 min at −100° C., ZnCl$_2$ (7.05 mL, 1M/Et$_2$O, 7.05 mmol) was added dropwise and the reaction mixture was warmed up to rt. A THF solution of 7-fluoro-2-oxo-2H-chromen-4-yl-trifluoromethanesulfonate (2.0 g, 6.41 mmol) and Pd(PPh$_3$)$_4$(0.370 g, 0.32 mmol) was added and the mixture was stirred at rt overnight. The mixture was partitioned between aqueous NaHCO$_3$ and EtOAc. The layers were separated and the aqueous phase was extracted with EtOAc. The combined organic layers were washed with brine and dried over anhydrous Na$_2$SO$_4$. The solvent was evaporated and the residue triturated in CH$_2$Cl$_2$ and acetone to give the title compound.

Step 2: 7-({5-[(1S)-hydroxy-1-(trifluoromethyl)propyl]-1,3-thiazol-2-yl}thio)-4-pyridin-3-yl-2H-chromen-2-one

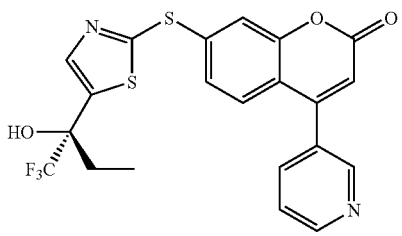

A mixture of 7-fluoro-4-pyridin-3-yl-2H-chromen-2-one (0.177 g, 0.73 mmol), (2S)-1,1,1-trifluoro-2-(2-mercapto-1,3-thiazol-5-yl)butan-2-ol (0.214 g, 0.88 mmol) and K$_2$CO$_3$ (0.203 g, 1.47 mmol) in NMP was heated at 120° C. overnight. The mixture was cooled to rt and partitioned between aqueous NH$_4$Cl and EtOAc. The layers were separated and the aqueous phase was extracted with EtOAc. The combined organic layers were washed with brine and dried over anhydrous Na$_2$SO$_4$. The solvent was evaporated and the residue chromatographed on silica gel (toluene/acetone; 95:5 to 80:20) to give the title compound. $^1$H NMR (400 MHz, CDCl$_3$): δ 8.81 (dd, 1H), 8.72 (dd, 1H), 7.82 (dt, 1H), 7.78 (s, 1H), 7.51-7.59 (m, 2H), 7.33-7.40 (m, 2H), 6.42 (s, 1H), 2.74 (br s, 1H), 2.12 (q, 2H), 0.99 (t, 3H).

EXAMPLE 25

4-(4-Fluorophenyl)-7-({5-[1-hydroxy-1-(trifluoromethyl)prop-2-en-1-yl]-1,3-thiazol-2-yl-}thio)-2H-chromen-2-one Step 1: 1,1,1-trifluoro-2-(2-mercapto-1,3-thiazol-5-yl)but-3-en-2-ol

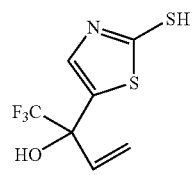

To a solution of vinyl iodide (1.88 g, 12.2 mmol) in Et$_2$O at −78° C. was added t-butyl lithium (14.3 ml, 1.7 M/pentane, 24.3 mmol). The mixture was stirred at −78° C. for 1 h and warmed up to −30° C. for 5 min. The mixture was cooled back to −78° C. and 2,2,2-trifluoro-1-(2-mercapto-1,3-thiazol-5-yl)ethanone (1.18 g, 5.53 mmol) in Et$_2$O was added. The reaction mixture stirred 30 min at −78° C., brought to 0° C. and partitioned between aqueous NH$_4$Cl and EtOAc. The layers were separated and the aqueous phase was extracted with EtOAc. The combined organic layers were washed with brine and dried over anhydrous Na$_2$SO$_4$. The solvent was evaporated and the residue chromatographed on silica gel (toluene/acetone; 90:10) to give the title compound.

Step 2: 4-(4-fluorophenyl)-7-({5-[1-hydroxy-1-(trifluoromethyl)prop-2-en-1-yl]-1,3-thiazol-2-yl}thio)-2H-chromen-2-one

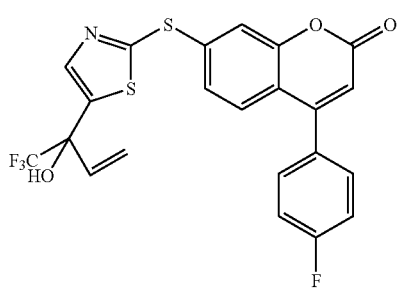

Employing the procedure of Example 1, Step 3, but using 1,1,1-trifluoro-2-(2-mercapto-1,3-thiazol-5-yl)but-3-en-2-ol, the title compound was obtained. $^1$H NMR (400 MHz, CDCl$_3$): δ 7.80 (s, 1H), 7.56 (d, 1H), 7.44-7.48 (m, 3H), 7.37 (dd, 1H), 7.24-7.26 (m, 2H), 6.40 (s, 1H), 6.32 (dd, 1H), 5.75 (d, 1H), 5.64 (d, 1H), 2.90 (br s, 1H).

EXAMPLE 26

7-({5-[1-Hydroxy-1-(trifluoromethyl)propyl]-1,3-thiazol-2-yl}thio)-4-(2-methyl-1,3-thiazol-4-yl)-2H-chromen-2-one Step 1:
7-bromo-4-(1-ethoxyvinyl)-2H-chromen-2-one

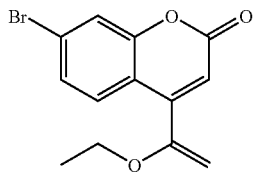

To a solution of triflate (compound V of Scheme 1) (5.1 g, 13.7 mmol) in dioxane was added tributyl(1-ethoxyvinyl)tin (4.8 mL, 14.2 mmol), (Ph₃P)₄Pd (0.790 g, 0.7 mmol) and LiCl (1.74 g, 41 mmol). The mixture was refluxed for 4 h, cooled and partitioned between aqueous NH₄Cl and EtOAc. The layers were separated and the aqueous phase was extracted with EtOAc. The combined organic layers were washed with brine and dried over anhydrous Na₂SO₄. The solvent was evaporated and the residue chromatographed on silica gel (CH₂Cl₂/EtOAc; 95:5) and triturated in hexane/Et₂O to give the title compound.

Step 2: 7-bromo-4-(bromoacetyl)-2H-chromen-2-one

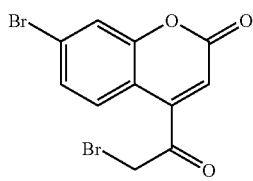

To a solution of 7-bromo-4-(1-ethoxyvinyl)-2H-chromen-2-one (2.0 g, 6.8 mmol) in THF and H₂O was added N-bromosuccinimide (1.3 g, 14.2 mmol) and stirred for 30 min. Toluene was added and the solvent was evaporated. The residue was chromatographed on silica gel (hexane/EtOAc; 80:20) to give the title compound.

Step 3: 7-bromo-4-(2-methyl-1,3-thiazol-4-yl)-2H-chromen-2-one

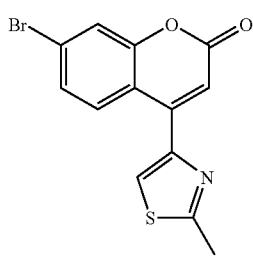

To a solution of 7-bromo-4-(bromoacetyl)-2H-chromen-2-one (0.605 g, 1.7 mmol) in DMF was added thioacetamide (0.138 g, 1.8 mmol). The mixture was stirred 24 h at rt and at 100° C. overnight. Once cool to rt, it was partitioned between aqueous NH₄Cl and EtOAc. The layers were separated and the aqueous phase was extracted with EtOAc. The combined organic layers were washed with brine and dried over anhydrous Na₂SO₄. The solvent was evaporated and the residue swished in hexanes/Et₂O to give the title compound.

Step 4: 7-({5-[1-hydroxy-1-(trifluoromethyl)propyl]-1,3-thiazol-2-yl}thio)-4-2-methyl-1,3-thiazol-4-yl)-2H-chromen-2-one

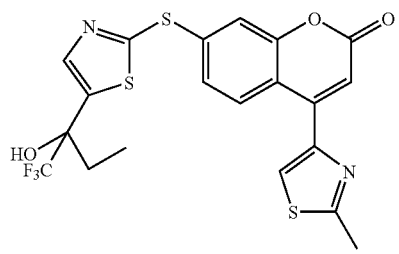

Employing the procedure of Example 1, Step 3, but using 7-bromo-4-(2-methyl-1,3-thiazol-4-yl)-2H-chromen-2-one, the title compound was obtained. ¹H NMR (400 MHz, CDCl₃): δ 8.18 (d, 1H), 7.76 (s, 1H), 7.53-7.60 (m, 2H), 7.42 (dd, 1H), 6.67 (s, 1H), 2.85 (s, 3H), 2.69 (br s, 1H), 2.11 (q, 2H), 0.98 (t, 3H).

EXAMPLE 27

4-(4-fluorophenyl)-7-({5-[(1R)-1-hydroxy-1-(trifluoromethyl)propyl}-1,3-thiazol-2-yl}sulfinyl)-2H-chromen-2-one

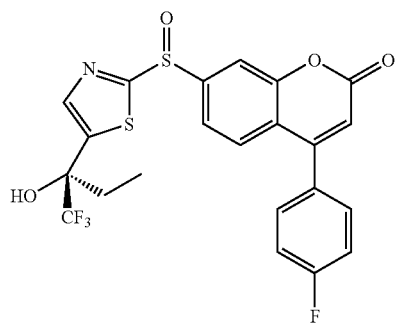

To a solution of 4-(4-fluorophenyl)-7-({5-[(1R)-1-hydroxy-1-(trifluoromethyl)propyl]-1,3-thiazol-2-yl}thio)-2H-chromen-2-one (0.100 g, 0.2 mmol) in 7 ml of CH₂Cl₂ and 0.7 ml of MeOH, was added magnesium monoperoxyphthalate hexahydrate (0.051 g, 0.1 mmol). The mixture was stirred at rt overnight and partitioned between water and CH₂Cl₂. The layers were separated and the organic phase washed with brine, dried over MgSO₄ and evaporated to dryness. The residue was chromatographed on silica gel (hexane/EtOAc; 8:2) to give two diastereoisomers. ¹H NMR (400 MHz, CDCl₃): δ 7.9 (s, 1H), 7.85 (s, 1H), 7.67 (dd, 2H), 7.45 (m, 2H), 7.25 (m, 2H), 6.47 (s, 1H), 2.12 (m, 2H), 0.92 (t, 3H). Diastereoisomer #2: ¹H NMR (400 MHz, CDCl₃): δ 7.9 (s, 1H), 7.82 (s, 1H), 7.67 (dd, 2H), 7.45 (m, 2H), 7.25 (m, 2H), 6.47 (s, 1H), 2.15 (m, 2H), 0.95 (t, 3H).

EXAMPLE 28

4-(4-fluorophenyl)-7-({5-[(1R)-hydroxy-1-trifluoromethyl)propyl}-1,3-thiazol-2-yl}sulfonyl)-2H-chromen-2-one

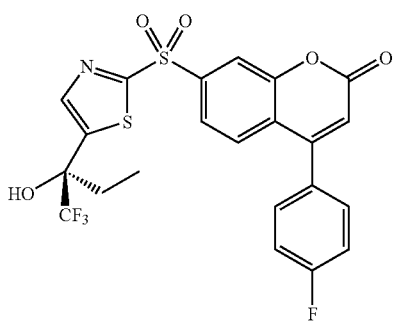

To a solution of 4-(4-fluorophenyl)-7-({5-[(1R)-1-hydroxy-1-(trifluoromethyl)propyl]-1,3-thiazol-2-yl}thio)-2H-chromen-2-one (0.050 g, 0.1 mmol) in 4 ml of $CH_2Cl_2$ and 0.4 mL of MeOH, was added magnesium monoperoxyphthalate hexahydrate (0.100 g, 0.2 mmol). The mixture was stirred at rt overnight and partitioned between water and $CH_2Cl_2$. The layers were separated and the organic phase washed with brine, dried over $MgSO_4$ and evaporated to dryness. The residue was chromatographed on silica gel (hexanes/EtOAc; 8:2) to give the title compound. $^1$H NMR (400 MHz, $CDCl_3$): δ 8.12 (s, 1H), 7.98 (d, 1H), 7.9 (s, 1H), 7.68 (d, 1H), 7.45 (m, 2H), 7.27 (m, 2H), 6.53 (s, 1H), 2.15 (m, 2H), 0.95 (t, 3H).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound of structural Formula I

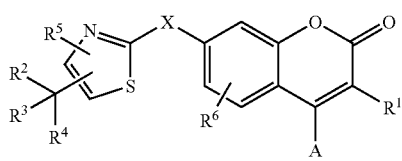

and the pharmaceutically acceptable salts and esters thereof wherein:

$R^1$ is selected from the group consisting of —H, —$C_{1-6}$alkyl and —$C_{3-6}$ cycloalkyl;

$R^2$ is selected from the group consisting of —H, —OH, —$OC_{1-3}$alkyl, —F and tetrazolyl, provided that when $R^2$ is tetrazolyl then neither $R^3$ nor $R^4$ is Z;

$R^3$ is selected from the group consisting of —H, —$CF_3$, —$CF_2CF_3$, —$C_{1-6}$alkyl, —$C_{1-6}$alkyl substituted with fluoro, —$C_{1-6}$alkyl-$R^7$, —$C_{2-6}$alkenyl, —$C_{3-6}$cycloalkyl, —$C_{5-7}$cycloalkenyl and -Z;

$R^4$ is selected from the group consisting of —H, —$CF_3$, —$CF_2CF_3$, —$C_{1-6}$alkyl, —$C_{1-6}$alkyl substituted with fluoro, —$C_{1-6}$alkyl-$R^7$, —$C_{2-6}$alkenyl, —$C_{3-6}$cycloalkyl, —$C_{5-7}$cycloalkenyl and -Z;

or $R^3$ and $R^4$ are joined together with the carbon to which they are attached to form a ring selected from the group consisting of a —$C_{3-6}$cycloalkyl ring and a —$C_{5-7}$cycloalkenyl ring, provided that when $R^3$ and $R^4$ are joined together with the carbon to which they are attached to form a —$C_{5-7}$cycloalkenyl ring, there is no double bond at the C1 position in the ring;

or $R^2$ and $R^3$ are joined together to form =$C_{1-6}$alkyl;

or $R^2$, $R^3$ and $R^4$ are joined together with the carbon to which they are attached to form a cycloalkenyl ring selected from:

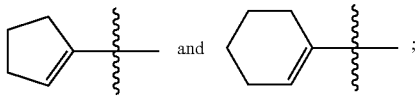

$R^5$ is selected from the group consisting of —H, —$C_{1-6}$ alkyl, —$C_{3-6}$ cycloalkyl and halo;

$R^6$ is selected from the group consisting of —H, —$C_{1-6}$ alkyl, —$C_{3-6}$ cycloalkyl and halo;

$R^7$ is selected from the group consisting of —$COOR^1$, —C(O)H, —CN, —$CR^1R^1OH$, —$OR^1$, —S—$C_{1-6}$ alkyl and —S—$C_{3-6}$ cycloalkyl;

A is selected from the group consisting of a) a 5-membered aromatic ring containing (i) one or more carbon atoms, (ii) one heteroatom selected from oxygen and sulfur, and (iii) zero, one, two or three nitrogen atoms, b) a 5-membered aromatic ring containing one or more carbon atoms and from one to four nitrogen atoms, c) a 6-membered aromatic ring containing carbon atoms and one, two or three nitrogen atoms;

d) a 6-membered aromatic ring selected from

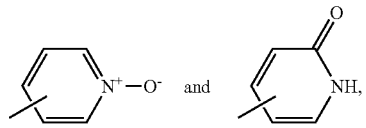

e) a bicyclic aromatic ring system selected from benzothienyl, indolyl, quinolinyl and naphthalenyl;

f) phenyl, g) —$CH_2$—$R^8$, wherein $R^8$ is selected from phenyl and dioxolanyl, h) —$C_{3-6}$cycloalkyl, i) —$C_{5-7}$cycloalkenyl, j) —$C_{1-6}$alkyl; and k) —$C_{2-6}$alkenyl, and wherein A is optionally mono- or di-substituted with a substituent independently selected at each occurrence from the group consisting of (i) halo, (ii) —OH, (iii) —$C_{1-3}$alkyl optionally substituted with one or more of halo, (iv) —$OC_{1-3}$alkyl optionally substituted with one or more of halo, (v) —$OC_{3-6}$cycloalkyl, (vi) —$CH_2OH$, (vii) —$COOR^1$, (viii) —CN and (ix) —$NR^9R^{10}$;

$R^9$ is selected from the group consisting of —H, —$C_{1-6}$ alkyl and —$C_{3-6}$ cycloalkyl;

$R^{10}$ is selected from the group consisting of —H, —$C_{1-6}$ alkyl, —$C_{3-6}$ cycloalkyl and —$COOR^1$;

X is selected from the group consisting of —S—, —SO— and —$SO_2$—; and

Z is selected from the group consisting of
  a) a 5-membered aromatic ring containing (i) one or more carbon atoms, (ii) one heteroatom selected from oxygen and sulfur, and (iii) zero, one, two or three nitrogen atoms,
  b) a 5-membered aromatic ring containing one or more carbon atoms and from one to four nitrogen atoms,
  c) a 6-membered aromatic ring containing carbon atoms and one, two or three nitrogen atoms;
  d) phenyl, and
  e) —$CH_2$—$R^8$, wherein $R^8$ is selected from phenyl and dioxolanyl, and wherein Z is optionally mono- or di-substituted with a substituent independently selected at each occurrence from the group consisting of (i) halo, (ii) —OH, (iii) —$C_{1-3}$alkyl optionally substituted with one or more of halo, (iv) —$OC_{1-3}$alkyl optionally substituted with one or more of halo, (v) —$OC_{3-6}$cycloalkyl, (vi) —$CH_2OH$, (vii) —$COOR^1$, (viii) —CN and (ix) —$NR^9R^{10}$.

2. The compound of claim 1 and the pharmaceutically acceptable salts and esters thereof wherein:

$R^1$ is selected from H and —$C_{1-6}$ alkyl;

$R^2$ is selected from the group consisting of —H, —OH and —F;

$R^3$ is selected from the group consisting of —$C_{1-6}$alkyl optionally substituted with fluoro, —$C_{1-6}$alkyl-$R^7$, and —$C_{3-6}$cycloalkyl;

$R^4$ is selected from the group consisting of —$C_{1-6}$alkyl optionally substituted with fluoro, —$C_{1-6}$alkyl-$R^7$, —$C_{2-6}$alkenyl, —$C_{3-6}$cycloalkyl and -Z;

or $R^3$ and $R^4$ are joined together with the carbon to which they are attached to form a —$C_{3-6}$cycloalkyl ring;

$R^5$ is selected from —H and —$CH_3$;

$R^6$ is selected from the group consisting of —H and —$CH_3$;

A is unsubstituted, mono- or di-substituted and is selected from the group consisting of:
  a) a 5-membered aromatic ring comprised of carbon, one heteroatom selected from —O— and —S—, and zero, one, two or three of —N—,
  b) a 5-membered aromatic ring comprised of carbon and from one to four of —N—,
  c) a 6-membered aromatic ring comprised of carbon and one, two or three of —N— and
  d) phenyl; and Z is unsubstituted, mono- or di-substituted and is selected from the group consisting of phenyl, benzyl, pyridinyl, thiazolyl, dioxolanyl and tetrazolyl.

3. The compound of claim 2 and the pharmaceutically acceptable salts and esters thereof wherein:

$R^3$ is selected from —$C_{1-2}$alkyl optionally substituted with fluoro and cyclopropyl;

$R^4$ is selected from —$C_{1-2}$alkyl optionally substituted with fluoro, cyclopropyl and Z;

A is unsubstituted, mono- or di-substituted and is selected from the group consisting of thienyl, furanyl, oxazolyl, thiazolyl, tetrazolyl, pyridinyl and phenyl; and Z is unsubstituted, mono- or di-substituted and is selected from the group consisting of phenyl, pyridinyl and thiazolyl.

4. The compound of claim 3 and the pharmaceutically acceptable salts and esters thereof wherein: $R^1$ is selected from —H and —$CH_3$; $R^2$ is selected from —H and —OH; $R^3$ is selected from —$CF_3$, —$CH_3$ and —$C_2H_5$ and cyclopropyl; $R^4$ is selected from —$CF_3$, —$CH_3$ and —$C_2H_5$ and cyclopropyl; $R^5$ is —H; $R^6$ is —H; and A is selected from phenyl, 3-fluorophenyl, 4-fluoro-phenyl, unsubstituted or mono-substituted thiazolyl, and unsubstituted or mono-substituted pyridinyl.

5. The compound of claim 1 of structural Formula Ia:

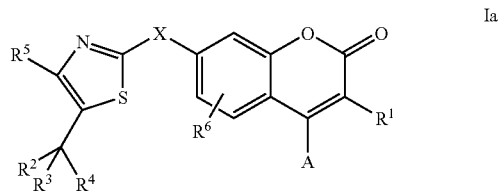

Ia and the pharmaceutically acceptable salts and esters thereof.

6. The compound of claim 1 of structural Formula Ib

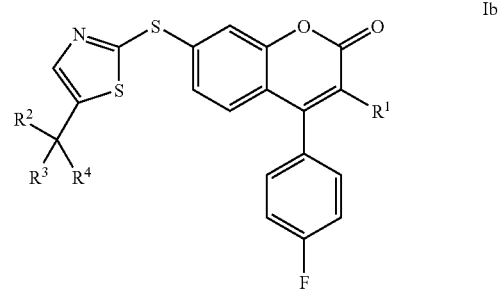

Ib and the pharmaceutically acceptable salts and esters thereof wherein:

$R^1$ is selected from the group consisting of —H and —$CH_3$;

$R^2$ is selected from the group consisting of —H and —OH;

$R^3$ is selected from the group consisting of —$CF_3$ and —$C_{1-6}$alkyl optionally substituted with fluorine;

$R^4$ is selected from the group consisting of —$CF_3$ and —$C_{1-6}$alkyl optionally substituted with fluorine;

or $R^3$ and $R^4$ are joined together with the carbon to which they are attached to form $C_{4-6}$cycloalkyl.

7. The compound of claim 1 selected from the group consisting of:

4-(4-fluorophenyl)-7-({5-[2,2,2-trifluoro-1-hydroxy-1-(trifluoromethyl)ethyl]-1,3-thiazol-2yl}thio)-2H-chromen-2-one;

4-phenyl-7-({5-[2,2,2-trifluoro-1-hydroxy-1-(trifluoromethyl)ethyl]-1,3-thiazol-2-yl}thio)-2H-chromen-2-one;

4-pyridin-3-yl-7-({5-[2,2,2-trifluoro-1-hydroxy-1-(trifluoromethyl)ethyl]-1,3-thiazol-2-yl}thio)2H-chromen-2-one;

4-(2-methyl-1,3-thiazol-4-yl)-7-({5-[2,2,2-trifluoro-1-hydroxy-1-(trifluoro-1-hydroxy-1-(trifluoromethyl)ethyl]-1,3-thiazol-2-yl}thio)-2H-chromen-2-one;

4-(4-fluorophenyl)-7-{[5-(1-hydroxycyclopentyl)-1,3-thiazol-2-yl]thio}-2H-chromen-2-one;

4-(2-methyl-1,3-oxazol-4-yl)-7-({5-[2,2,2-trifluoro-1-hydroxy-1-(trifluoromethyl)ethyl]-1,3-thiazol-2-yl}thio)-2H-chromen-2-one;

4-(4-fluorophenyl)-7-({5-[1-hydroxy-1-(trifluoromethyl)propyl]-1,3-thiazol-2-yl}thio)-2H-chromen-2-one;

4-(1,3-thiazol-4-yl)-7-({5-[2,2,2-trifluoro-1-hydroxy-1-(trifluoromethyl)ethyl]-1,3-thiazol-2-yl}thio)-2H-chromen-2-one;

(−)-7-{[5-(1-cyclopropyl-2,2,2-trifluoro-1-hydroxyethyl)-1,3-thiazol-2-yl]thio}-4-(4-fluorophenyl)-2H-chromen-2-one;

(+)-7-{[5-(1-cyclopropyl-2,2,2-trifluoro-1-hydroxyethyl)-1,3-thiazol-2-yl]thio}-4-(4-fluorophenyl)-2H-chromen-2-one;

7-({5-[(1S)-1-hydroxy-1-(trifluoromethyl)propyl]-1,3-thiazol-2-yl}thio)-4-phenyl-2H-chromen-2-one;

7-({5-[dicyclopropyl(hydroxy)methyl]-1,3-thiazol-2-yl}thio)-4-phenyl-2H-chromen-2-one;

7-({5-[dicyclopropyl(hydroxy)methyl]-4-methyl-1,3-thiazol-2-yl}thio)-4-pyridin-3-yl-2H-chromen-2-one;

7-{[5-(dicyclopropylmethyl)-1,3-thiazol-2-yl]thio}-4-(4-fluorophenyl)-2H-chromen-2-one;

7-{[5-(dicyclopropylmethyl)-1,3-thiazol-2-yl]thio}-4-pyridin-3-yl-2H-chromen-2-one;

7-{[5-(1-cyclopropyl-2,2,2-trifluoro-1-hydroxyethyl)-1,3-thiazol-2-yl]thio}-4-(3-methylphenyl)-2H-chromen-2-one;

7-({5-[dicyclopropyl(hydroxy)methyl]-1,3-thiazol-2-yl}thio)-4-(2-methyl-1,3-thiazol-4-yl)-2H-chromen-2-one;

7-({5-[dicyclopropyl(hydroxy)methyl]-1,3-thiazol-2-yl}thio)-4-pyrimidin-5-yl-2H-chromen-2-one;

(−)-(R)-4-(4-fluorophenyl)-7-({5-[1-hydroxy-1-(trifluoromethyl)propyl]-1,3-thiazol-2-yl}thio)-2H-chromen-2-one;

7-({5-[(1R)-1-hydroxy-1-(trifluoromethyl)propyl]-1,3-thiazol-2-yl}thio)-4-(3-methylphenyl)-2H-chromen-2-one;

(+)-7-{[5-(1-cyclopropyl-2,2,2-trifluoro-1-hydroxyethyl)-1,3-thiazol-2-yl]thio}-4-pyridin-3-yl-2H-chromen-2-one;

(−)-7-{[5-(1-cyclopropyl-2,2,2-trifluoro-1-hydroxyethyl)-1,3-thiazol-2-yl]thio}-4-pyridin-3-yl-2H-chromen-2-one;

7-({5-[(1R)-1-hydroxy-1-(trifluoromethyl)propyl]-1,3-thiazol-2-yl}thio)-4-pyridin-3-yl-2H-chromen-2-one;

7-({5-[(1S)-1-hydroxy-1-(trifluoromethyl)propyl]-1,3-thiazol-2-yl}thio)-4-pyridin-3-yl-2H-chromen-2-one;

7-({5-[dicyclopropyl(hydroxy)methyl]-1,3-thiazol-2-yl}thio)-4-pyridin-3-yl-2H-chromen-2-one; and the pharmaceutically acceptable salts and esters thereof.

8. The compound of claim 1 selected from the group consisting of:

(−)-(R)-4-(4-fluorophenyl)-7-({5-[1-hydroxy-1-(trifluoromethyl)propyl]-1,3-thiazol-2-yl}thio)-2H-chromen-2-one;

(+)-7-{[5-(1-cyclopropyl-2,2,2-trifluoro-1-hydroxyethyl)-1,3-thiazol-2-yl]thio}-4-pyridin-3-yl-2H-chromen-2-one;

(−)-7-{[5-(1-cyclopropyl-2,2,2-trifluoro-1-hydroxyethyl)-1,3-thiazol-2-yl]thio}-4-pyridin-3-yl-2H-chromen-2-one;

4-(4-fluorophenyl)-7-{[5-(1-hydroxycyclopentyl)-1,3-thiazol-2-yl]thio}-2H-chromen-2-one;

(−)-7-{[5-(1-cyclopropyl-2,2,2-trifluoro-1-hydroxyethyl)-1,3-thiazol-2-yl]thio}-4-(4-fluorophenyl)-2H-chromen-2-one;

(+)-7-{[5-(1-cyclopropyl-2,2,2-trifluoro-1-hydroxyethyl)-1,3-thiazol-2-yl]thio}-4-(4-fluorophenyl)-2H-chromen-2-one;

7-({5-[(1S)-1-hydroxy-1-(trifluoromethyl)propyl]-1,3-thiazol-2-yl}thio)-4-phenyl-2H-chromen-2-one;

7-({5-[dicyclopropyl(hydroxy)methyl]-1,3-thiazol-2-yl}thio)-4-phenyl-2H-chromen-2-one;

7-{[5-(dicyclopropylmethyl)-1,3-thiazol-2-yl]thio}-4-pyridin-3-yl-2H-chromen-2-one;

7-({5-[dicyclopropyl(hydroxy)methyl]-1,3-thiazol-2-yl}thio)-4-(2-methyl-1,3-thiazol-4-yl)-2H-chromen-2-one;

7-({5-[(1R)-1-hydroxy-1-(trifluoromethyl)propyl]-1,3-thiazol-2-yl}thio)-4-pyridin-3-yl-2H-chromen-2-one;

7-({5-[(1S)-1-hydroxy-1-(trifluoromethyl)propyl]-1,3-thiazol-2-yl}thio)-4-pyridin-3-yl-2H-chromen-2-one;

7-({5-[dicyclopropyl(hydroxy)methyl]-1,3-thiazol-2-yl}thio)-4-pyridin-3-yl-2H-chromen-2-one;

and the pharmaceutically acceptable salts and esters thereof.

9. A pharmaceutical composition comprising a therapeutically effective amount of a compound of claim 1 and a pharmaceutically acceptable carrier.

10. The pharmaceutical composition of claim 9 additionally comprised of a therapeutically effective amount of a lipid altering compound.

* * * * *